US009453833B2

(12) United States Patent
Dimitrov

(10) Patent No.: US 9,453,833 B2
(45) Date of Patent: Sep. 27, 2016

(54) SYSTEM AND METHOD FOR DETECTING AND MONITORING PROTEOLYSIS OF PROTEIN MATRICES

(71) Applicant: Digital Diagnostics Pty. Ltd., Sherwood, Queensland (AU)

(72) Inventor: Krassen Dimitrov, Jhubei (TW)

(73) Assignee: Digital Diagnostics Pty. Ltd., Sherwood (AU)

( * ) Notice: Subject to any disclaimer, the term of this patent is extended or adjusted under 35 U.S.C. 154(b) by 0 days.

(21) Appl. No.: 14/145,986

(22) Filed: Jan. 1, 2014

(65) Prior Publication Data
US 2014/0134659 A1 May 15, 2014

Related U.S. Application Data

(63) Continuation-in-part of application No. 13/978,702, filed as application No. PCT/AU2011/001672 on Dec. 22, 2011.

(30) Foreign Application Priority Data

Jan. 7, 2011 (AU) ................................ 2011900035

(51) Int. Cl.
| | | |
|---|---|---|
| *G01N 33/487* | (2006.01) | |
| *G01N 33/49* | (2006.01) | |
| *C12Q 1/00* | (2006.01) | |
| *C12Q 1/56* | (2006.01) | |

(52) U.S. Cl.
CPC ............... *G01N 33/49* (2013.01); *C12Q 1/005* (2013.01); *C12Q 1/56* (2013.01); *G01N 33/48707* (2013.01)

(58) Field of Classification Search
None
See application file for complete search history.

(56) References Cited

U.S. PATENT DOCUMENTS

| | | | |
|---|---|---|---|
| 4,699,876 A | 10/1987 | Libeskind | |
| 5,385,846 A | 1/1995 | Kuhn et al. | |
| 5,909,114 A | 6/1999 | Uchiyama et al. | |
| 6,046,051 A | 4/2000 | Jina | |
| 2005/0186635 A1* | 8/2005 | Bamdad ................ | B82Y 15/00 435/7.1 |
| 2008/0096495 A1* | 4/2008 | Shen .................... | G06F 19/3418 455/100 |
| 2009/0060999 A1 | 3/2009 | Lyngstadaas et al. | |
| 2011/0250616 A1 | 10/2011 | Bamdad et al. | |

FOREIGN PATENT DOCUMENTS

| | | |
|---|---|---|
| AU | 2005203615 A1 | 9/2005 |
| EP | 1 482 296 A1 | 12/2004 |
| JP | 60-176589 A | 9/1985 |
| JP | 2005-83928 A | 3/2005 |
| JP | 2009-244013 A | 10/2009 |
| JP | 2009-264920 A | 11/2009 |
| KR | 10-0945571 B1 | 3/2010 |
| WO | WO 2009/064983 A1 | 5/2009 |
| WO | 2012/092646 A1 | 7/2012 |
| WO | 2013/039362 A2 | 3/2013 |

OTHER PUBLICATIONS

Kumar et al. "Smart polymers: Physical forms and bioengineering applications." (2007) Progress in Polymer Science, vol. 32: 1205-1237.*
Stoller et al. "Best practice methods for determining an electroade material's performance for ultracapacitors." (2010) Energy & Environmental Science, vol. 3: 1294-1301.*
Baş et al., "Rapid Method for Quantitative Determination of Proteolytic Activity with Cyclic Voltammetry," *Electroanalysis* 22(3):265-267, 2010.
Extended European Search Report, dated Apr. 7, 2014, for corresponding EP Application No. 11854784.3-1408 / 2661633, 5 pages.
International Search Report and Written Opinion, mailed Apr. 17, 2015, for corresponding International Application No. PCT/US2014/073030, 16 pages.
Ryan et al., "Influence of a Natural and a Synthetic Inhibitor of Factor XIIIa on Fibrin Clot Rheology," *Biophysical Journal* 77: 2827-2836, Nov. 1999.
Official Action from Patent Office of Australia, mailed Jul. 25, 2016, for Patent Application No. 2011354498, 10 pages.

* cited by examiner

*Primary Examiner* — Robert Yamasaki
*Assistant Examiner* — Teresa E Knight
(74) *Attorney, Agent, or Firm* — Seed IP Law Group PLLC

(57) ABSTRACT

Apparatus and methods are provided for detecting and monitoring proteolysis of protein matrices such as fibrin clots, extracellular matrix and collagen matrix. The apparatus and methods involve in general the measurement of diffusion-limited electrochemical currents generated by an electroactive species or elactomer in a synthetic protein matrix. The apparatus and methods are applied in various embodiments to detect and monitor the proteolytic activities of a sample, and more specifically fibrinolytic activities and collagenase activities of a sample. The apparatus and methods are utilized generally in the monitoring and diagnostics of cardiovascular, cerebralvascular, and oncology conditions.

21 Claims, 13 Drawing Sheets

A.

B.

C.

D.

A.

B.

| Gold chip2, E6 (given by SR on 17 Sep 10) | Amperometric response |
|---|---|
| Before clotting | 6.5 e-6 A |
| After clotting and incubation | 2.1 e-6 A |
| After plasmin addition and 7 min incubation | 3.4 e-6 A |

A.

B.

C.

A.

B.

C.

D.

A.

B.

C.

D.

E.

F.

G.

SYSTEM AND METHOD FOR DETECTING AND MONITORING PROTEOLYSIS OF PROTEIN MATRICES

This application claims the priority benefit from U.S. patent application Ser. No. 13/978,702 (the "'702 application"), the national phase of PCT/AU2011/001672, which was filed Oct. 18, 2013 (371 (c) date) and entitled "Proteolysis Detection." This application is a continuation-in-part of the '702 application.

BACKGROUND OF THE DISCLOSURE

The present disclosure relates in general to analytical instruments and methods for electrochemical testing. Specifically, the present disclosure relates to electrochemical detection of proteolysis of proteinaceous matrices. More specifically, new apparatus and methods are provided for detecting proteolysis of proteinaceous matrices including fibrin clots, extracellular matrix and similar collagen or related protein-based matrices, whether endogenous or synthetic.

Protein matrices are important for tissue function, tissue regeneration, wound healing, and hemostasis, among other things. For example many eukaryotic cells are enveloped by an extracellular matrix of proteins that provide structural support, cell and tissue identity, and autocrine, paracrine and juxtacrine properties for the cell and the matrix is thus required for normal tissue functions. In wound healing a cascade of molecular and cellular events initially lead to homeostasis, the prevention of blood loss. Fibrin plays a crucial role in hemostasis and wound healing as it forms a crosslinked proteinaceous matrix (clot) by means of a complex cascade of reactions with the final steps being the conversion of monomeric fibrinogen by thrombin, to form a crosslinked fibrin polymer, which is often referred to as a clot.

In addition to its role in hemostasis fibrin formation is common in a number of pathological and inflammatory conditions. For example, fibrin deposition (thrombosis) is associated with atherosclerosis, rheumatoid arthritis, glomerulonephritis, systemic lupus erythematosus, myocardial infarcts, pulmonary embolism, deep vein thrombosis, autoimmune neuropathies, granulomatous disease, parasitic infections and allograft rejection. There is also evidence that thrombosis plays a role in neurodegenerative disease. Similarly, collagenases play significant role in invasive cancer where they degrade the extracellular matrix in healthy tissues to allow primary tumor cells to escape their primary environment and subsequently invade distant tissues to form distant metastases.

Interestingly, protein matrices such as extracellular matrix and fibrin clots are typically dynamic, that is the matrix can be formed and degraded as part of pathological processes or normal physiological processes. Indeed, hemostasis can be viewed as the maintenance of an equilibrium between the formation of fibrin clots and the proteolytic degradation of those clots (fibrinolysis) by enzymes or coagulation factors including plasmin.

Methods for detecting or monitoring the formation of protein matrices such as blood clots (thrombi) include for example methods of determining blood coagulation e.g., prothrombin time, thrombin clotting time or the Clauss method for fibrinogen testing, and there are commercial devices that can perform such coagulation testing in portable, point-of-care formats. However, tests for detecting or monitoring fibrinolysis are generally limited to complex methodologies in specialized laboratories and on native fibrin clots, such as, for example thromboelastometry (TEM), and are not applicable to point of care or field diagnostics. Alternative approaches employ colorimetric or fluorescent detection methodologies and are, too, expensive, complex and furthermore negatively affected by the color or turbidity of a sample, and hence ineffective for timely and sensitive detection and monitoring of fibrinolysis.

There therefore exists a need for new and improved apparatus and methods for detecting and/or monitoring proteolysis of protein matrices. In particular, for example, electrochemical and related analytical technology which detect and monitor proteolysis activities such as fibrinolysis or the breakdown of collagen, extracellular matrix, or other similar protein matrices, may provide valuable diagnostics and monitoring tools for medicine and wellness.

SUMMARY OF THE VARIOUS EMBODIMENTS

It is therefore an object of this disclosure to provide new and improved systems and methods for the detection and monitoring of physiologically and pathologically relevant proteolysis activities of endogenous or synthetic protein matrices. It is a further object of this disclosure to provide new and improved systems and methods that enables detection and monitoring of proteolysis activities such as fibrinolysis or the breakdown of collagen and extracellular matrix.

According to one embodiment, there is provided an apparatus for detecting or monitoring proteolysis of a protein matrix, comprising (i) a synthetic protein matrix, (ii) a working electrode, and (iii) a counter electrode, wherein the synthetic protein matrix is in contact with at least a portion of each of the electrodes, wherein a first and second electroactive species are provided in contact with the synthetic protein matrix, wherein upon exposure to a sample, diffusion-limited electrochemical currents are generated by the first electroactive species at the working electrode and counter currents are generated by the second electroactive species at the counter electrode, and the diffusion-limited electrochemical currents are measured, the measurement being indicative of a level of proteolysis of the synthetic protein matrix.

In another embodiment, the synthetic protein matrix is one of fibrin clot, blood clot, platelet rich plasma clot, gelatin, collagen matrix, and the matrix is formed on, within, or around a support. In yet another embodiment, the working electrode is larger than the counter electrode. In a further embodiment, the first and second electroactive species are the opposite oxidation states of the same molecule.

In a particular embodiment, the first electroactive species a is an elactomer, as defined and disclosed herein. In one embodiment, the elactomer is one of polyethylene glycols (PEGs), Polyvinyl alcohol (PVA), polypeptide, polyamine, and derivatives thereof. In another embodiment, the second electroactive species is a small molecule electroactive species, and the diffusivity of the second electroactive species is different than that of the elactomer. In yet another embodiment, the relative concentrations of the first and second electroactive species are determined such that essentially all of the current at the working electrode are generated by the first electroactive species, and not by the second electroactive species. In a further embodiment, the first electroactive species is PEG-Fc (Fc-CO—NH—(CH2CH2O)n-NH—CO-Fc) and the second electroactive species is ruthenium (III) hexamine (Ru(NH3)63+).

In one embodiment, the sample is one of blood, plasma, interstitial fluid, other bodily fluid, and a control sample with known proteolytic activity.

In another embodiment, the apparatus further comprises a data processing unit adapted to analyze the measurement of the diffusion limited currents using a predetermined formula or methodology, thereby producing a result indicative of proteolysis of the protein matrix. In yet another embodiment, the apparatus further comprises an output unit adapted to output said measurement of the diffusion limited currents and the result is indicative of proteolysis. In a further embodiment, one of the data processing and output units is one of mobile devices or mobile apps.

In one embodiment, the counter electrode comprises a reference electrode and an auxiliary electrode.

According to another embodiment, there is provided a method for detecting or monitoring proteolytic activity of a sample, comprising (i) providing a synthetic protein matrix subject to the proteolytic activity, the synthetic protein matrix in contact with a working electrode and a counter electrode, (ii) providing a first and second electroactive species in contact with the synthetic protein matrix, (iii) exposing the synthetic protein matrix to the sample, whereby diffusion-limited electrochemical currents are generated by the first electroactive species at the working electrode and counter currents are generated by the second electroactive species at the counter electrode, (iv) measuring the diffusion-limited electrochemical currents the measurement being indicative of a level of the proteolytic activity in the sample.

According to a further embodiment, there is provided a method for detecting or monitoring fibrinolytic activity of a sample, comprising (i) providing a synthetic fibrin strip, the strip having printed thereon a working electrode and a counter electrode, (ii) providing an elactomer and a small-molecule electroactive species in contact with the synthetic protein matrix, (iii) exposing the fibrin strip to the sample, whereby diffusion-limited electrochemical currents are generated by the elactomer at the working electrode and counter currents are generated by the small-molecule electroactive species at the counter electrode, (iv) measuring the diffusion-limited electrochemical currents, the measurement being indicative of a level of fibrinolytic activity in the sample.

According to another embodiment, there is provided a method for detecting or monitoring collagenase activity of a sample, comprising (i) providing a gelatin strip, the strip having printed thereon a working electrode and a counter electrode, (ii) providing an elactomer and a small-molecule electroactive species in contact with the protein matrix, (iii) exposing said gelatin strip to the sample, whereby diffusion-limited electrochemical currents are generated by the elactomer at the working electrode and counter currents are generated by the small-molecule electroactive species at the counter electrode, (iv) measuring the diffusion-limited electrochemical currents, the measurement being indicative of a level of collagenase activity in the sample.

According to yet another embodiment, the measurement of diffusion-limited electrochemical currents from the sample is indicative of a baseline, and the method further comprises exposing a second synthetic protein matrix to a second sample, and measuring diffusion-limited electrochemical currents from the second sample. The differences between the baseline and the second are indicative of changes in proteolytic activities according to this embodiment.

In various embodiments, the measuring is based on one of chronoamperometry, potential step voltammetry, linear sweep voltammetry, cyclic voltammetry, square wave voltammetry, staircase voltammetry, anodic or cathodic stripping voltammetry, adsorptive stripping voltammetry, alternating current voltammetry, rotated electrode voltammetry, normal or differential pulse voltammetry, and chronocoulometry.

In another embodiment, the measuring is conducted on alternating currents or multiple direct current pulses. In yet another embodiment, the measuring is based on electrochemical impedance spectroscopy, whereby changes in a frequency domain are indicative of a level of proteolytic activity in the sample.

DETAIL DESCRIPTION OF THE VARIOUS EMBODIMENTS

I. Definitions

Unless otherwise defined herein, various terms referenced in this disclosure shall have their established meanings understood by the person of skill in the art. For clarity, the below terms are defined as follows for the purpose of this disclosure.

As used in this application, the singular form "a", "an" and "the" include plural references unless the context clearly dictates otherwise. For example, the term "matrix" or "proteinaceous matrix" also includes a plurality of matrices or proteinaceous matrices respectively. Unless the context requires otherwise or specifically stated to the contrary, integers, steps, or elements of the invention recited herein as singular integers, steps or elements clearly encompass both singular and plural forms of the recited integers, steps or elements.

By "about" is meant a measurement, quantity, level, activity, value, number, frequency, percentage, dimension, size, amount, weight or length that varies by as much as 10, 9, 8, 7, 6, 5, 4, 3, 2 or 1% to a reference measurement, quantity, level, activity, value, number, frequency, percentage, dimension, size, amount, weight or length.

The terms "biological sample" as used herein refers to a sample that may be extracted, untreated, treated, diluted or concentrated from a subject. The biological sample may include a biological fluid such as whole blood, serum, plasma, saliva, urine, sweat, ascitic fluid, peritoneal fluid, synovial fluid, amniotic fluid, cerebrospinal fluid, tissue biopsy, lymph fluid, interstitial fluid, and the like. In certain embodiments, the biological sample comprises blood.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The term "electroactive species" as used herein is defined as a substance that may be oxidized or reduced and that may transfer one or more electrons. An electroactive species is a reagent in an electrochemical analysis and provides for the indirect measurement of the proteolysis of a proteinaceous matrix. Generally, "electroactive species" reduce or oxidize in aqueous solutions at potentials below those required for electrolysis of water, thereby being active in conditions where water electrolysis does not generate significant Faradic currents.

Figure 6:
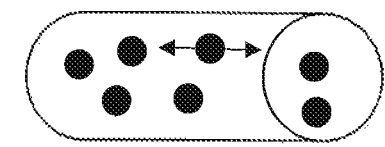
FIG. 6 depicts according to one embodiment, the diffusion of a polymer electroactive species or an elactomer (bottom), within and across the pores of a proteinaceous matrix or hydrogel, contrasted with the diffusion of a small molecule electroactive species (top) within or across the pores of a proteinaceous matrix or hydrogel.
Figure 6:
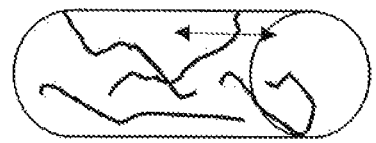

The term "elactomer" as used herein means electroactive polymer or polymer electroactive species. An elactomer is an electroactive species according to certain embodiments of this disclosure, and refers to various electroactive polymers including for example polyethylene glycols (PEGs), Polyvinyl alcohol (PVA), polyamines, polypeptides, and suitable derivatives thereof. An illustration of an elactomer compared to a small-molecule electroactive species is shown in FIG. 6 below.

The term "redox pair" as used herein refers to two conjugate species of a chemical substance having different oxidation numbers. Reduction of the species having the higher oxidation number produces the species having the lower oxidation number. Alternatively, oxidation of the species having the lower oxidation number produces the species having the higher oxidation number.

The term "proteolysis" as used herein refers to the breakdown, of proteins into smaller polypeptides and the resulting degradation of protein fibers. The breakdown may occur by cleavage of peptide bonds due to enzymatic or chemical mechanisms. The breakdown may occur by cleavage of crosslinks between homologous or heterologous proteins. Proteolysis may result in breakdown of the protein into individual amino acids.

The term "electrode" as used herein means an electric conductor through which a potential can be measured. An electrode can also be a collector and/or emitter of an electric current. Preferably, an electrode is a solid and comprises a conducting metal. Preferable conducting metals include alloys such as indium tin oxide, conductive carbon, or noble metals such as gold, silver, palladium or platinum. An electrode can also be a wire or microwire, or the term "electrode" can describe a collection of wires or microwires.

II. Components and Aspects of the Various Embodiments

1. Proteinaceous Matrices

The proteinaceous matrices of the invention may be any protein matrix known in the art. The terms "proteinaceous matrix" and "protein matrix" are interchangeable as used herein. According to the various embodiments, the protein matrix may exist naturally such as extracellular matrix or may be formed naturally, such as by coagulation of blood or the action of thrombin on fibrinogen. In some embodiments a synthetic proteinaceous matrix is formed in vitro. In some embodiments the proteinaceous matrix is formed from one or more proteins that spontaneously form the matrix. In some embodiments the proteinaceous matrix is formed by reaction of proteins with one or more polyanions and/or crosslinking agents. In some embodiments the proteinaceous matrix is a fibrin matrix formed by contacting fibrinogen with thrombin. In other embodiments, the proteinaceous matrix is a collagen matrix (e.g., native or reconstituted aggregations of type I collagen molecules).

Biological fluids may be reacted with certain agents to form protein matrices. The biological fluids may be blood, plasma, serum, urine, cerebrospinal fluid, tears, saliva, milk, mucus, sputum, peritoneal cavity fluid. Alternatively, such fluids may be synthetically prepared compositions, e.g., tissue culture medium, tissue culture medium containing proteins, synthetic polymers, polymers with functional groups found on proteins such as amines, sulfhydryl, carboxyls or hydroxyls, amine-terminated polyethylene glycol, amine-terminated polyethers, or mixtures of thereof. Non-limiting examples of proteins suitable for use in preparing protein matrices include fibrinogen, fibrin, collagen, fibronectin, and laminin Methods for making such matrices are well known in the art.

In some embodiments the proteinaceous matrix comprises non-protein components such as cells, lipids, carbohydrates, sugars, salts and the like.

The proteinaceous matrix generally substantially inhibits diffusion of an electroactive species. From physical perspective the protein fibers in the proteinaceous matrix interact to form a porous viscoelastic substance with very high dynamic viscosity (e.g., >2 Pas). From Einstein-Stokes equation, the diffusion constant, D, is given by $$D = \frac{k_B T}{6\pi \eta r}$$

where η is the dynamic viscosity. When the protein fibers in the matrix are broken down proteolytically, the porosity of the matrix increases, the viscosity decreases, and the diffusion constant increases.

The proteinaceous matrix may be subjected to a mechanical or physical treatment. The mechanical treatment may include compression or extrusion.

In some embodiments, the proteinaceous matrix comprises an electroactive species that is capable of being oxidized or reduced to form a charged species. Non-limiting examples of electroactive species include ferricyanide, ferrocyanide, decamethylferrocene (DMFc), 1,1'-dimethylferrocene (DiMFc) and 7,7,8,8-tetracyanoquinodimethane (TCNQ), ferrocene carboxylic acid, ruthenium hexamine.

In specific embodiments, the proteinaceous matrix is subjected to dehydration. In these embodiments, the proteinaceous matrix is suitably rehydrated when contacted with a sample (e.g., a biological sample) under test. The dehydration can be performed in an oxygen-containing atmosphere (e.g., air), or in an inert atmosphere, such as a nitrogen atmosphere. Desirably, the dehydration is selected from lyophilization (i.e., freeze drying), heat dehydration (e.g., at ambient temperature), osmosis, filtration and centrifugation. After dehydration, the proteinaceous matrix desirably has a low moisture content, for example a moisture content of less than about 7.5%, less than about 2%, less than about 1%.

In some embodiments, the proteinaceous matrix is a fibrin clot, PRP clot or blood clot, and the proteolytic activity in the sample is provided at least in part by plasmin. In other embodiments the proteinaceous matrix is collagen, and the proteolytic activity in the sample is provided at least in part by one or more collagenases (e.g., matrix metalloproteases (MMPs) such as MMP-1, MMP-8, MMP-13, MMP-18 etc.).

The proteinaceous matrix may be attached to or formed on an electrode (e.g., working electrode) using conventional methods known to persons of skill in the art, such as for example by screen printing, or ink-jet printink, or robotic pipetting.

2. Proteinaceous Matrix Supports

In various embodiments there are also provides a support for and relating to a proteinaceous matrix. The support may be a porous support. It will be understood that the pores of the support may be substantially interconnecting and/or and extend through the volume of the support. In other embodiments the pores may be substantially unconnected and extend through the volume of the support. Preferably at least a portion of the proteinaceous matrix is contained in the pores. Illustrative examples of porous supports include papers such as sorbents, filter paper, filter membranes, sintered glass, poly(vinylidene fluoride) membranes, and gels. The proteinaceous matrix-containing solid supports of the present invention are especially advantageous as they can be manufactured in large quantities with greater consistency in pore size and pore volume of one and preferably both of the solid support and the proteinaceous matrix, which suitably improves inter or intra-assay reliability and consistency.

In specific embodiments, the solid supports are porous. Illustrative porous solid supports have a structure comprising pores of a diameter that is substantially greater than the pore diameter of the proteinaceous matrix. For example, the pore at least about 5.0 µm, at least about 10.0 µm, and is suitably 20 µm or more as larger pores are less restrictive to diffusion of an electroactive species.

In some embodiments, the solid supports further comprise an electroactive species that is capable of being oxidized or reduced to form a charged species (e.g., ferricyanide, ferrocyanide, decamethylferrocene (DMFc), 1,1'-dimethylferrocene (DiMFc), 7,7,8,8-tetracyanoquinodimethane (TCNQ) ferrocene carboxylic acid, ruthenium hexamine etc).

The proteinaceous matrix-containing solid supports may be subjected to a mechanical or physical treatment. The mechanical treatment may include compression or extrusion. Representative physical treatments include dehydration (e.g., lyophilization, heat dehydration etc.) and radiation (e.g., light). The mechanical or physical treatment is suitably carried out under sterile conditions.

In specific embodiments, the solid supports are subjected to dehydration, thereby resulting in solid supports that are in substantially dehydrated form. In these embodiments, the solid supports are suitably rehydrated when contacted with a sample (e.g., a biological sample) under test. The dehydration can be performed in an oxygen-containing atmosphere (e.g., air), or in an inert atmosphere, such as a nitrogen atmosphere. Desirably, the dehydration is selected from lyophilization (i.e., freeze drying), heat dehydration (e.g., at ambient temperature), osmosis, filtration and centrifugation. After dehydration, the solid supports desirably have a low moisture content, for example a moisture content of less than about 7.5%, less than about 2%, less than about 1%, or less than about 0.5%. Dehydration of the solid supports has several advantages including reducing degradation and improving shelf life of the proteinaceous matrix. It also permits better or more efficient contact of a putatively protease-containing sample with the proteinaceous via capillary flow or 'wicking' of the sample therethrough.

In some embodiments, the solid support is attached to an electrode (e.g., a working electrode) using conventional methods known to persons of skill in the art such as adhesion with adhesives or thermal bonding.

3. Synthetic Fibrin Clot

In certain embodiments there is provided a synthetic fibrin clot as a proteinaceous matrix applied in the methods, systems, and kits disclosed herein. According to one embodiment, a fibrin clot or "mesh" is prepared by a process that comprises: (a) providing a first component comprising a fibrinogen-containing material; (b) providing a second component comprising a substance that converts fibrinogen into a fibrin clot; (c) forming a fibrin clot-containing material by combining and mixing the first component with the second component; and (d) contacting the fibrin clot-containing material with at least a portion of an electrode.

The first component suitably comprises a fibrinogen-containing solution comprising at least about 2 mg/mL, at least about 5 mg/mL, or at least about 10 mg/mL fibrinogen, desirably at least about 15 mg/mL, for example from about 20 mg/mL to about 250 mg/mL or from about 20 mg/mL to about 150 mg/mL fibrinogen.

The second component suitably comprises a solution comprising thrombin. A volume of the thrombin-comprising solution is contacted with the first component to provide a final thrombin concentration/activity of less than about 1000 IU/mL, less than about 200 IU/mL, less than about 100 IU/mL, less than about 50 IU/mL, less than about 20, less than about 10 IU/mL or less than about 1 IU/mL. The thrombin can be in an active or inactive form and it is well known in the art that when thrombin is in an inactive form (e.g., a thrombin that can be activated for example by radiation or light (=photoactivatable thrombin), a larger amount of it is generally required to clot a sample of thrombin than the thrombin in an active form. The thrombin can be recombinant or synthetic or of natural origin, i.e. derived from human or animal plasma.

The synthetic fibrin clot in some embodiments has a pore diameter that substantially inhibits diffusion of an electroactive species (e.g., $K_3Fe(CN)_6$). In non-limiting examples, the pore diameter of the fibrin clot is less than about 100 nanometers (nm), less than about 5.0 nm, less than about 2.0 nm, and is suitably 1.0 nm or less.

The fibrin clot-containing material includes within its scope 'naked' fibrin clots as well as those contained or otherwise associated with a porous solid support. Acceptable supports for use in the present invention can vary widely and can be synthetic or natural, organic or inorganic, flexible or nonflexible. Representative supports include polymeric supports, such as woven and nonwoven webs (e.g., fibrous webs), microporous fibers and microporous membranes as well as particulate or beaded supports. Woven and nonwoven webs may have either regular or irregular physical configurations of surfaces.

Illustrative porous solid supports have a structure comprising pores of a diameter that is greater than the pore diameter of the fibrin clot. For example, the pore diameter is at least about 1.0 micrometer (µm), at least about 5.0 µm, at least about 10.0 µm, and is suitably 20 µm or more as larger pores are less restrictive to diffusion of an electroactive species. Non-limiting examples of porous supports include filter paper, sintered glass, poly(vinylidene fluoride) membrane, particulate or beaded supports such as agarose, hydrophilic polyacrylates, polystyrene, mineral oxides and Sepharose.

Suitably, the fibrin clot-containing material (e.g., naked or contained or otherwise associated with a porous solid support) is subjected to a mechanical or physical treatment. The mechanical treatment may include compression or extrusion. Representative physical treatments include dehydration (e.g., lyophilization, heat dehydration etc.) and radiation (e.g., light). The mechanical or physical treatment is suitably carried out under sterile conditions.

In specific embodiments, the fibrin clot-containing material comprises an electroactive species that is capable of being oxidized or reduced to form a charged species (e.g., ferricyanide, ferrocyanide, decamethylferrocene (DMFc), 1,1'-dimethylferrocene (DiMFc), 7,7,8,8-tetracyanoquinodimethane (TCNQ) etc.).

In certain embodiments, the fibrin clot-containing material is subjected to dehydration. In these embodiments, the fibrin clot-containing material is suitably rehydrated when contacted with a sample (e.g., a biological sample) under test. The dehydration can be performed in an oxygen-containing atmosphere (e.g., air), or in an inert atmosphere, such as a nitrogen atmosphere. Desirably, the dehydration is selected from lyophilization (i.e., freeze drying), heat dehydration (e.g., at ambient temperature), osmosis, filtration and centrifugation. After dehydration, the fibrin clot-containing material suitably has a low moisture content, for example a moisture content of less than about 7.5%, less than about 2%, less than about 1%, or less than about 0.5%. In specific embodiments, the fibrin clot-containing material is subjected to lyophilization so as to prepare a dry or substantially dry porous support that comprises a fibrin clot.

The fibrin clot-containing material (e.g., naked or contained or otherwise associated with a porous solid support) is attached to the electrode using conventional methods known to persons of skill in the art.

4. Detection of Proteolysis of Protein Matrices

According to certain embodiments, proteolysis of protein matrices is detected by electrochemical methods including voltammetry. Voltammetry is a technique typically used to investigate mechanisms of electrolysis but as disclosed herein finds application in detecting or monitoring proteolysis of proteinaceous matrices, particularly in response to proteolysis. Various forms of voltammetry may be used in the detection; these forms include square wave voltammetry, staircase voltammetry, anodic or cathodic stripping voltammetry, adsorptive stripping voltammetry, alternating current voltammetry, rotated electrode voltammetry, normal or differential pulse voltammetry, chronoamperometry, chronocoulometry, or current versus time. In exemplary embodiments of the methods and systems of this disclosure, potential step voltammetry, linear sweep voltammetry and cyclic voltammetry are utilized. Either peak current, or steady state current, or total charge transferred may be used as a measurement variable.

In each of these types of voltammetry a voltage or series of voltages are applied to an electrode known as the working electrode and the corresponding current that flows is monitored. Typically the working electrode contacts an electroactive species, for example ferricyanide ($Fe(CN)_6^{3-}$) and a potential is applied to facilitate the transfer of charge to and from the electroactive species, thereby generating a current. A second electrode acts as the other half of an electrolytic cell. The role of the second electrode is to supply or subtract electrons to thereby maintain electroneutrality in the solution. If correct estimation of the potential at the working electrode-relative to a known standard is required, the second electrode can be divided between two separate electrodes, the reference electrode and the auxiliary electrode.

The reference electrode is a half-cell with a known reduction potential and which acts as reference in measuring and controlling the working electrodes potential and does not pass current. The auxiliary electrode passes the current needed to balance the current observed at the working electrode.

Thus the elements needed for an electrolysis measurement by voltammetry are at least two electrodes, a solvent, a background electrolyte and an electroactive species. The two electrodes are typically in contact with a solvent comprising the electrolyte and the electroactive species.

In certain embodiments a protein matrix is in contact with or present on at least a portion of a working electrode such that the mobility or diffusion of an electroactive species to the working electrode to transfer charge to or from that electrode is impaired or prevented. In other embodiments a protein matrix is present on at least a portion of the second electrode and its ability to balance the charge added or removed by the working electrode is impaired or prevented. In further embodiments a protein matrix is present on at least a portion of the working and the second electrodes. In these embodiments, the current measured on application of a potential is altered in comparison to the absence of a protein matrix. Accordingly, when the protein matrix is contacted with a proteolytic agent for example by addition of such an agent or a sample putatively containing such an agent to the solvent or directly to the protein matrix, degradation of the protein matrix occurs. As the protein matrix is proteolyzed the current measured on application of a potential also changes thereby allowing qualitative and/or quantitative detection and/or monitoring of the degradation of a protein matrix.

The background electrolyte is an electrochemically inert salt such as aqueous solution of sodium chloride. In some embodiments, physiological fluid (0.9% sodium chloride) can be used as background electrolyte. The electroactive species typically present in low concentrations (in the order of 0.01, 0.02, 0.03, 0.04, 0.05, 0.06, 0.07, 0.08, 0.09 or 0.1M). The electroactive species may be for example ferricyanide $(Fe(CN)_6^{3-})$.

The electroactive species is capable of being oxidized or reduced to form a charged species. That is the electroactive species forms a redox pair, for example when ferricyanide is the electroactive species a ferricyanide $(Fe(CN)_6^{3-})$/ferrocyanide $(Fe(CN)_6^{4-})$ redox pair. The electroactive species can be oxidized or reduced at the working electrode on application of a potential, thus causing electrochemical current in the working electrode. In some embodiments the electroactive species undergoes reversible oxidation or reduction. The electroactive species is preferably chemically stable.

According to one embodiment, potential step voltammetry is employed where the applied voltage is switched or stepped from one value $(V_1)$ to another $(V_2)$. The resulting current is then measured as a function time. For example, using ferricyanide as the reactant the voltage range is typically set such that at V1 the reduction of $(Fe(CN)_6^{3-})$ is thermodynamically unfavorable. The second voltage $(V_2)$ is typically selected so that any $Fe(CN)_6^{3-}$ close to the electrode surface is reduced to product $(Fe(CN)_6^{4-})$.

In potential step voltammetry the current rises immediately after the switch (step) in voltage and then decreases over time. This occurs because before the voltage step the electrode is in contact with the electroactive species in the electrolytic solution has a constant composition however, once the voltage step occurs the electroactive species (e.g., $Fe(CN)_6^{3-}$) is converted to product (e.g., $Fe(CN)_6^{4-}$) and current flows. For the reaction to continue further electroactive species (e.g., $Fe(CN)_6^{3-}$) must approach the electrode. This typically occurs in solution by diffusion which is dependent on the concentration gradient of the electroactive species. So the supply of further electroactive species to the surface, and thus the flow of current, depends on the diffusional flux of the electroactive species.

As the electrolysis continues electroactive species diffuses from greater distances from the electrode and therefore the concentration gradient drops, thus the supply of electroactive species to the electrode surface also drops, consequently the current decreases.

The current can be calculated using the formula $$i = nFAk_{red}c^{bulk}\sqrt{\frac{D}{\pi t}} \propto t^{-1/2}$$

Where i is current, n is the number of moles of electrons transferred in the reaction, F is Faraday's constant (96,484 C mol$^{-1}$), A is the electrode area, $k_{red}$ is the rate constant for electron transfer, $c^{bulk}$ is the total concentration of the electroactive species, t is time and D is the diffusion coefficient of the electroactive species The current is related to the bulk concentration of the electroactive species which is the combined concentration of the reduced and oxidized species. Step voltammetry thus allows the estimation of the diffusion coefficients of the electroactive species. Consequently in embodiments where the diffusion of an electroactive species is affected by the presence of a proteinaceous matrix estimations of the change in diffusion coefficients for example due to the proteolysis of a proteinaceous matrix can be used to detect of monitor the proteolysis of the proteinaceous matrix.

According to another embodiment, linear sweep voltammetry (LSV) is employed where a fixed potential range is applied although the voltage is scanned from a lower limit $(V_1)$ to an upper limit $(V_2)$. The characteristics of the linear sweep voltammogram depend on a number of factors including the rate of the electron transfer reaction(s), the chemical reactivity of the electroactive species and the voltage scan rate.

In LSV as the voltage is swept to more reductive values a current begins to flow and eventually reaches a peak before dropping. At the electrode surface the rate of electron transfer is fast in comparison to the voltage sweep rate and at the electrode surface an equilibrium is established substantially the same as that predicted by thermodynamics. As the voltage is initially swept from $V_1$ the equilibrium at the surface begins to alter and the current begins to flow. The current rises as the voltage is swept further from its initial value as the equilibrium is shifted and more electroactive species is reduced. A peak in the current occurs when the diffusion layer has grown sufficiently above the electrode so that the flux of electroactive species to the electrode is not fast enough to satisfy that required by the Nernst equation when the current begins to drop. The Nernst equation describes the relationship between the voltage of an electrochemical cell and the concentration of one of the components of the cell as follows.

$$E_{cell} = E^0_{cell} - (RT/nF)\ln Q$$

Where $E_{cell}$ is the cell potential after application of a potential to one electrode, $E^0_{cell}$ is the cell potential prior to applying the potential, R is the gas constant (8.31 (volt-coulomb)/(mol-K), T is the temperature (K), n is the number of moles of electrons exchanged in the electrochemical reaction (mol), F is Faraday's constant (96,484 C mol$^{-1}$) and Q is the reaction quotient (the equilibrium expression with initial concentrations rather than equilibrium concentrations The size of the diffusion layer above the electrode surface will be different depending upon the voltage scan rate used. In a slow voltage scan the diffusion layer will grow much further from the electrode in comparison to a fast scan. Consequently the flux to the electrode surface is considerably smaller at slow scan rates than it is at faster rates. As the current is proportional to the flux towards the electrode, the magnitude of the current will be lower at slow scan rates and higher at high rates.

The term "linear scan" is defined as a scan where the voltage is varied in a single "forward" direction at a fixed scan rate, such as from −0.7 V to +0.7 V against Ag/AgCl to provide a 1.4 V scan range A linear scan may be approximated by a series of incremental changes in potential. If the increments occur very close together in time, they correspond to a continuous linear scan. Thus, applying a change of potential approximating a linear change may be considered a linear scan.

During a linear scan the current at the working electrode is measured while the potential at the working electrode changes linearly with time at a constant rate. The scan range, such as from about −0.5 V to about +0.5 V from about −1.0 V to +1.0 V typically covers the reduced and oxidized states of a redox pair of the electroactive species so that a transition from one state (e.g., reduced) to the other (e.g., oxidized) occurs.

In certain embodiments the voltage is changed at a rate of at least about 10 mV/sec, or at least about 50 mV/sec, or at least about 100 mV/sec, or at least about 150 mV/sec, or at least about 200 mV/sec, or at least about 500 mV/sec, or at least about 1000 mV/sec, or at least about 2000 mV/sec.

According to a further embodiment, cyclic voltammetry (CV) is employed. CV is very similar to LSV although the voltage is swept or scanned in a cyclic manner (cyclic scan) between two values at a fixed rate, however now when the voltage reaches $V_2$ the scan is reversed and the voltage is swept back to $V_1$. The forward sweep produces an identical response to that seen in LSV experiment as the electroactive species is reduced. When the scan is reversed reduced electroactive species is oxidized and the current flow is reversed.

The term "cyclic scan" refers to a combination of a linear forward scan and a linear reverse scan where the scan range includes the oxidation and reduction peaks of a redox pair. For example, varying the potential in a cyclic manner from about −1.0 V to about +1.0 V and back to about −1.0 V is an example of a cyclic scan for the ferricyanide/ferrocyanide redox pair, where both the oxidation and reduction peaks are included in the scan range.

5. Polymer Electroactive Species (Elactomer)

Generally protein matrices may be viewed as monophasic viscoelastic systems. However, some protein matrices according to certain embodiments are considered bi-phasic systems comprising a polymer backbone as the first phase, which is immersed in a liquid as the second phase. The first phase polymer backbone may be rigid or elastic, and the second phase liquid may be water or other suitable solvents. Such matrices are also referred to as hydrogels according to certain embodiments and consistently with the relevant art.

The diffusion of an electroactive species through a hydrogel is a complex process that cannot be easily modelled through the dynamic viscosity of the system as a whole. Factors affecting the diffusion coefficient (D) in such porous hydrogels are the porosity (the fraction of solvent occupying the hydrogel, it is a measure of how much space is available for diffusion), constrictivity (a measure of how tightly the solvent is ordered in the pore, due to interactions with pore walls), tortuosity (a measure of how pore geometry affects diffusion), and interactivity with the matrix (a measure of how weak bonds and Van der Walls interactions with the scaffold affect D)

If, for example, (i) the hydrogel has very high porosity, (ii) the electroactive species does not interact or does not form weak bonds with the protein molecules, (ii) the water in the pores has the same degree of ordering as in free solution, and (iv) the pore tortuosity is low, then the electroactive species will diffuse through the pore system with a diffusion coefficient that is very close to the diffusion in the solvent itself.

In one embodiment, there is provided a new electroactive species which is referred to as elactomer in this disclosure. Elactomers are polymers themselves, which may be utilized to determine hydrogel porosity with high sensitivity according to certain embodiments. Such determination are conducted by measuring the diffusion-limited electrochemical current with electrochemical techniques, including without limitation chronoamperometry and linear-scan voltammetry. In situations where the protein matrix is being proteolytically degraded, the matrix porosity increases as a function of proteolysis and the elactomer may be used to measure proteolysis according to a particular embodiment.

The diffusion of a polymer electroactive species or elactomer is more sensitive to the hydrogel porosity than that of a small-molecule or ion electroactive species, due to entanglement of the elactomer with the polymer scaffold, entropic pore confinement effects, and/or steric hindrance effects.

In one embodiment, the elactomers include ferrocene-derivitized polyethylene glycols (PEGs). Ferrocene and its derivatives are electroactive organic compounds, which can be used for derivatization of larger molecules, based on established organic chemistry processes. For example, ferrocenoyl chloride—the acyl chloride of ferrocene-carboxylic acid—is highly reactive to primary amines and can be used to effectively derivatize large molecules with primary amines.

Ferrocene by itself, is highly hydrophobic, and will not be readily soluble by itself in aqueous solutions. In contrast, PEGs are highly hydrophilic polymers, which are very compatible with biological applications and will mix well into the proteinaceous matrices, without causing protein denaturation or aggregation.

According to one embodiment, a homobifunctional amino PEG with molecular weight may be modified at both amino-groups with ferrocenoyl-chloride and the resulting product may be confirmed by IR-spectroscopy. An advantage of using a homobifunctional PEG with primary amino groups at the ends is that the resulting molecule is still highly hydrophilic and dissolves easily in aqueous solutions. Alternative approaches, where ferrocene can be added as pendant moieties onto internal monomeric groups in the polymer, would result in a highly derivitized hydrophobic molecule.

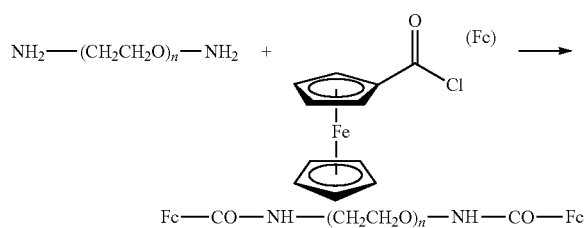

In another embodiment, the elactomers may be similarly derived from other water-soluble macromolecules, including polyvinyl alcohols (PVAs), polyvinyl pyrrolidones (PVPs), polyacrylates, polysaccharides such as dextrans, polyamines, polypeptides or proteins.

6. Composition of Electroactive Species

In certain embodiments chronoamperometric measurements are used in the method and system of this disclosure, as are other voltammetric measurements. As is known to the ordinary skill in the art, chronoamperometric measurements have been used in medical diagnostics, for example in glucose level determination, where electrochemical current at a particular time point is measured. For simplicity and low cost, often these measurements have been made in a two-electrode cell, without a reference electrode. In such setups, a potential is applied across the two electrodes and current is measured at the working electrode. To maintain electroneutrality, thus, an equal-in magnitude-current would be supplied at the other (counter) electrode.

According to one embodiment of this disclosure, when using chronoamperometry among other techniques as discussed herein to measure diffusion-limited currents in protein matrices to determine matrix porosity and viscosity as well as proteolytic degradation thereof, a sufficient level of current is supplied at the counter electrode (CE), such that the current provided to the working electrode (WE) is diffusion-limited, and the overall current through the system is not constrained at the counter-electrode. In certain embodiments, the WE is significantly larger than the CE, so that more WE area is exposed to the sample (i.e. blood or interstitial fluid) to provide for stronger signal to be measured. Based on the Cottrell equation the smaller CE area would restrict the CE current, which needs to be counteracted either through a larger reactant concentration at the CE ($C_0$), or through faster diffusion of the CE reactant (D).

In some embodiments the above requirement is met with the same electroactive species in opposite oxidation states, undergoing oxidation (reduction) at the WE and reduction (oxidation) at the CE, respectively. According to these embodiments, the concentration of the oxidized (reduced) form, which represents the reactant of the CE reaction is substantially higher than the reduced (oxidized) form, which represents the reactant at the WE. This ensures that sufficient current is provided at the CE.

In other embodiments where elactomers are used in protein matrices, however, the above approach to deal with the CE current restriction issue may be impractical. Due to the high molecular weight, having a significant excess of elactomers of the opposite oxidation state in the protein matrix may greatly increase the total mass of the polymer, where the elactomer itself may cause material increase and distort the viscosity and porosity of the matrix, thereby interfering with measurement.

Therefore there is provided in another embodiment a composition of mixed electroactive species, comprising a first electroactive species being an elactomer for determination of diffusion-limited current at the WE, and a second electroactive species being a small-molecule electroactive species for supplying sufficient counter-current at the CE. The first electroactive species is referred to herein also as the working electroactive species (WES), whereas the second electroactive species is also referred to as the counter electroactive species (CES). According to this embodiment, the excess small-molecule CES does not increase the overall polymer content or the viscosity of the matrix. Further, due to its smaller molecular weight, the CES at the CE has higher diffusion coefficient, which according to the Cottrell equation results in higher current. Consequently, the CES is supplied not in significant excess relative to the WES according to this embodiment, compared to the situation where both electroactive species have the same diffusivity.

Because the WES and CES are of opposing oxidation states, they may oxidize/reduce each other based on their standard redox potentials and concentrations (activities) until a Nernst equilibrium is reached. This may result in substantial quantities of the CES in the opposite oxidation state to the one that was initially supplied. This in turn may generate a corresponding current at the working electrode, interfering with the signal from the WES. Therefore, according to this embodiment, the WES and CES and their relative concentrations are determined in a manner to ensure that most to essentially all of the current at the WE be generated by the WES, and little to essentially none be generated by the CES. A particular example of the workings of the WES and CES is set forth below in Example II.

III. Systems and Methods According to the Various Embodiments

1. Methods for Detecting and Monitoring Proteolysis

In various embodiments, there are provided methods for detecting and/or monitoring the degradation of proteinaceous matrices, particularly due to proteolysis. In further, methods are provided to detect and/or monitor the proteolytic activity of a sample, e.g., fribrinoytic activity or collagenase activity of a sample.

The methods typically comprise providing a first electrode, a second electrode and an electrolytic solution comprising an electroactive species wherein a proteinaceous matrix is disposed on or in contact with at least a portion of at least the first electrode. When a potential is applied through the electrolytic solution a current is generated. When the potential is altered the current is also altered and the change in current as a function of voltage is measured at a number of time points. If the proteinaceous matrix is degraded, for example due to proteolysis the change in current as a function of voltage will be altered compared to a baseline or control measurement (typically charge versus current) where no degradation of the matrix has occurred. Typically the density of the proteinaceous matrix severely inhibits diffusion of the electroactive species. Degradation of the matrix, for example by fibrinolysis decreases the density of the matrix and the typically decreases the degree of cross-linking, thus the effective dynamic viscosity decreases leading to an increase in the apparent diffusion coefficient within the matrix or the porous support comprising the matrix and hence allows a change in electrochemical current.

A "baseline" is a control measurement and in some embodiments is a normal current measurements against which a test sample can be compared. Therefore, it can be determined, based on the control or baseline current measurement whether a sample has a measurable increase, decrease, or substantially no change in matrix degradation, as compared to the baseline level. In one aspect, the baseline level can be indicative of the absence of proteolytic activity, in particular the fibrinolytic activity in a subject. Therefore, the term "proteolytic activity" used in reference to a baseline level of current measurements typically refers to a baseline level established either in the absence of a sample from a subject or a population of subjects or in the presence of a sample from a subject or a population of subjects which is believed to have normal proteolytic activity and/or fibrinolytic activity. In another embodiment, the baseline can be established from a previous sample from a subject, so that the proteolytic activity of a subject can be monitored over time and/or so that the efficacy of a given therapeutic or pharmacologic agent can be evaluated over time.

The method for establishing a baseline is preferably the same method that will be used to evaluate the sample from the subject. In one embodiment, the baseline level is established using the same sample type as the sample to be evaluated.

In one embodiment, the baseline is established in an autologous control sample obtained from the subject. That is, the sample is obtained from the same subject from which the sample to be evaluated is obtained. The control sample is preferably the same sample type as the sample to be evaluated.

The methods may involve detecting or monitoring the proteolytic activity in a subject or a sample from the subject sample using any voltammetric method known in the art such as for example potential step voltammetry, linear sweep voltammetry or cyclic voltammetry. The proteolytic activity may be compared to a predetermined or reference charge versus current measurements to distinguish a normal subject from a subject with abnormal proteolytic activity.

The voltammetric method may be repeated with the same proteinaceous matrix with for example 10 to 180 seconds waiting period between measurements. During that time a proteolytic reaction for example a plasmin fibrinolytic reaction may continue and at each time point the current response will be altered compared to previous measurements, typically the response will be more pronounced. For example, a ratio of the 10 sec, 30 sec, 60 sec or 180 sec current signal to the initial (t=0) current can be used as a measurement parameter. In this way the impact of the other parameters (active electrode surface area, WES concentration, porous support variability) are internally controlled for, as they do not change between the two time points. The only variable is the degree of degradation of the proteinaceous matrix such as proteolysis, e.g., fibrinolysis.

The proteinaceous matrix may be formed directly on the electrode. Alternatively the proteinaceous matrix may be formed in solution or on a surface and at least one electrode subsequently placed in contact with the matrix. In certain embodiments the proteinaceous matrix is formed, at least partially in a porous support and at least one electrode placed in contact with the matrix. For example the matrix may be formed by applying a solution of protein, such as fibrinogen to the porous support and subsequently applying a polyanion, crosslinking agent or additional protein such as thrombin to the support to facilitate formation of the matrix. The porous support may then be applied to at least a portion of an electrode or the electrode inserted into the support.

In one embodiment at least one electrode having a protein matrix disposed on at least a portion of its surface may be inserted into a sample putatively having proteolytic activity.

In another embodiment the electrode is in contact with the proteinaceous matrix and a voltammetric measurement is taken, typically this is a measurement of a change in current as a function of voltage (e.g., charge versus current). Subsequent to this a sample is applied to the porous support and further voltammetric measurements taken wherein a difference between measurements taken before and after the application of the sample are indicative of the sample having proteolytic activity.

The sample may be biological sample such as bodily fluid, excretion or secretion. For example the sample may be selected from selected from the group comprising, saliva, blood, blood plasma, blood serum, or interstitial fluid.

The sample may be obtained from a subject with a disease or condition. In some embodiments the disease or condition may be associated with fibrin deposition. These diseases or conditions include deep vein thrombosis, pulmonary embolism, renal disease, hypertrophic keloid scars, coronary infarction, metastasis, inflammation, disseminated intravascular coagulation, atherosclerosis, rheumatoid arthritis, glomerulonephritis, systematic lupus erythematosus, autoimmune neuropathies, granulomatous disease, parasitic infection and allograft rejection.

In other embodiments the sample may be obtained from a subject before, during or after the administration of a therapeutic agent or a treatment regimen such as those therapies or treatment regimes used in the above diseases or conditions. In such embodiments the samples are subject to voltammetric measurements as described herein as a means to detect or monitor the effect of the therapeutic agent or a treatment regimen on the ability of the subject to degrade proteinaceous matrices. For example in embodiments where the proteinaceous matrix is a fibrin clot the methods may be used to detect or monitor the effect of the therapeutic agent or a treatment regimen on the subject's fibrinolytic activity.

In a further embodiment, a gelatin matrix over a support is formed as a strip where a blood or interstitial fluid sample containing gelatin degrading enzymes (a.k.a. gelatinases, collagenase, or matrix metalloproteases) is added. The ensuing proteolysis of the matrix increases the matrix porosity and decreases the overall effective viscosity, resulting in an increase in D, and hence increase in the diffusion-limited electrochemical current.

The collagen proteolysis detection method of this embodiment may be applied to monitor for cancer metastases, for both prognosis and prevention purposes according to various embodiments. Collagenases play significant role in invasive cancer where they degrade the extracellular matrix in healthy tissues to allow primary tumor cells to escape their primary environment and subsequently invade distant tissues to form distant metastases.

The collagenase activity in peripheral blood and particular locales in the body varies from person to person. For example, other processes such as wound repair that require tissue remodeling are associated with extracellular matrix breakdown. The detection method described herein provide for easy, sensitive and convenient monitoring of collagenase activity in blood and other bodily fluid such as interstitial fluid according to various embodiments. See example II below for additional discussions Importantly, persistent increase in collagenase activity over time in a particular individual would signal the possible presence of invasive cancer and allow for further diagnostic tests and appropriate therapy on time.

2. Systems and Apparatus for Detecting and Monitoring Proteolysis

In certain embodiments, there is provided an apparatus for use in the detection and/or monitoring of degradation of protein matrices. The apparatus typically comprises at least electrode and a proteinaceous matrix, and it may be utilized as a clinical and medical device or home-use monitoring device in various embodiments. In some embodiments the apparatus is provided as a point-of-care device or wellness monitoring tool. The matrix is typically in contact with at least a portion of the electrode.

In some embodiments the matrix may be formed directly on the electrode, for example by placing the electrode or a portion thereof in contact with a solution comprising at least one protein at least one polyanion and/or at least one crosslinking agent such that the matrix forms on the electrode. Alternatively the matrix may be formed on the electrode by placing the electrode in contact with a solution comprising components that will form a matrix, for example a solution of fibrinogen and thrombin or a sample of blood.

In certain embodiments, to perform the aforementioned methods there are provided a system for performing the detection and/or monitoring of proteolysis of a proteinaceous matrix. In certain embodiments, such detection or monitoring are performed using voltammetric techniques. The system according to this embodiment comprises means for voltammetric analysis including a working electrode, a counter electrode, a current measurement unit, a control unit, a data storage unit and a data processing unit. The counter electrode may include a reference electrode and an auxiliary electrode. In one aspect, the working and/or counter electrodes may be at least partially coated with a proteinaceous matrix such as a fibrin clot.

In one embodiment working electrode is typically connected to a first potential supplied by a controllable variable potential source, such as those known in the art or commercially available potential sources. The current measurement unit is arranged to register the current flowing between the working electrode and the counter electrode and the current measured by the current measurement unit is used as an indicator of the proteolysis of the protein matrix. In one embodiment, the current measurement unit comprises a current amplifier that produces an output representative of the measured current.

The control unit is typically arranged to control the second potential, the working electrode and the counter electrode and to read current values from the current measurement unit at predetermined times. In methods using cyclic voltammetry, a control cycle comprises, setting the second potential, controlling the working electrode and counter electrodes and reading current values from the current measurement unit. The control unit can comprise a memory unit wherein control software is stored, or a control-interface which is controlled by an external process control system.

Figure 4:
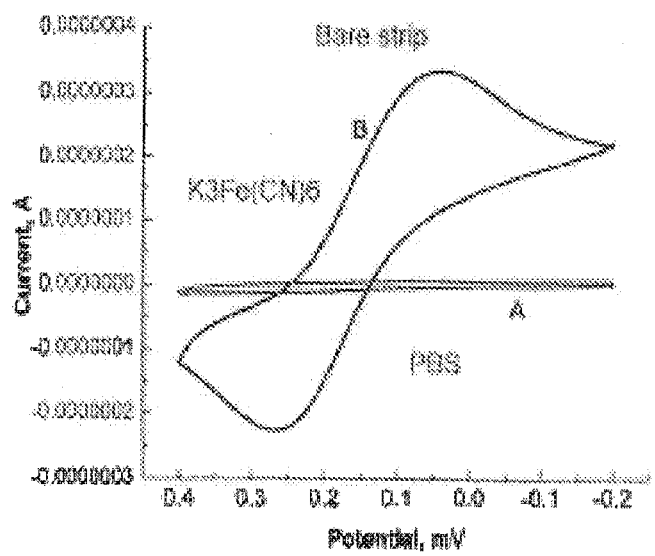
FIG. 4 depicts according to another embodiment, (A) a cyclic voltammogram of a Whatmann grade 113 filter paper strip with PBS or PBS with 10 mM ferricyanide (Fe(CN)6); (B) a current versus time plot for a 0.2% fibrin clot in Whatmann grade 113 filter paper in the presence of 10 mM Fe(CN)6 and a current versus time plot for a 0.2% fibrin clot in Whatmann grade 113 filter paper in the presence of 10 mM Fe(CN)6 and plasmin; (C) a current versus time plot for a 0.2% fibrin clot in Whatmann grade 113 filter paper in the presence of 10 mM Fe(CN)6; (D) a current versus time plot for a 0.2% fibrin clot in Whatmann grade 113 filter paper in the presence of 10 mM Fe(CN)6 and plasmin.
Figure 4:
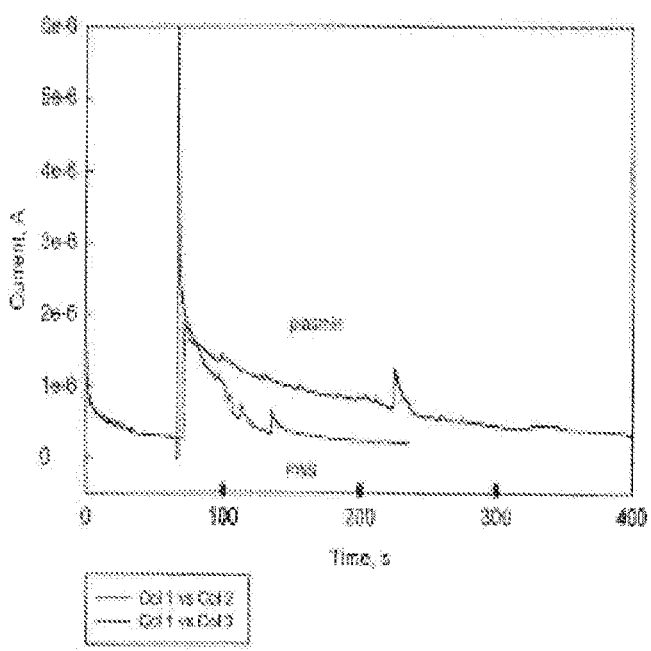
Figure 4:
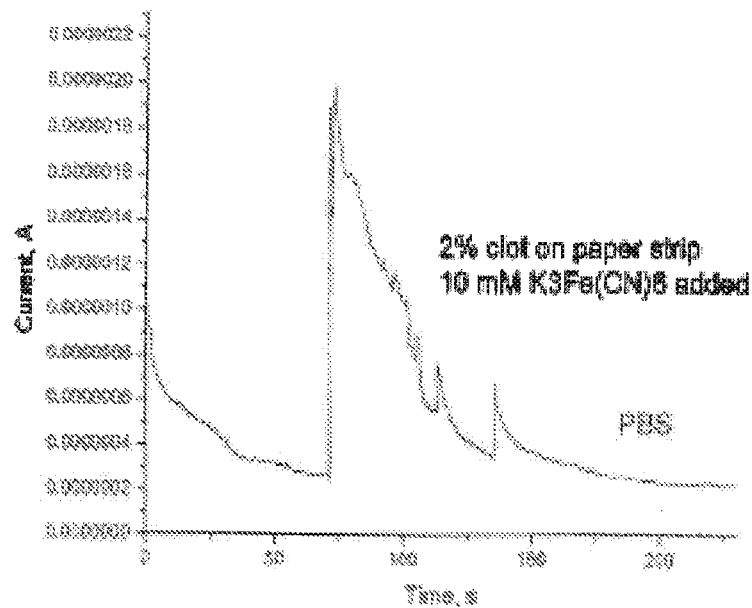
Figure 4:
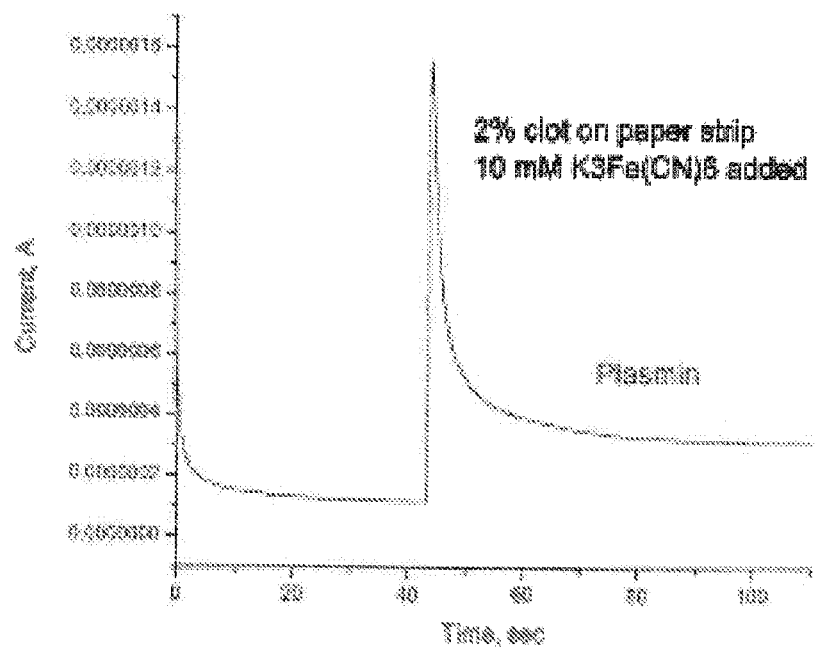
Figure 5:
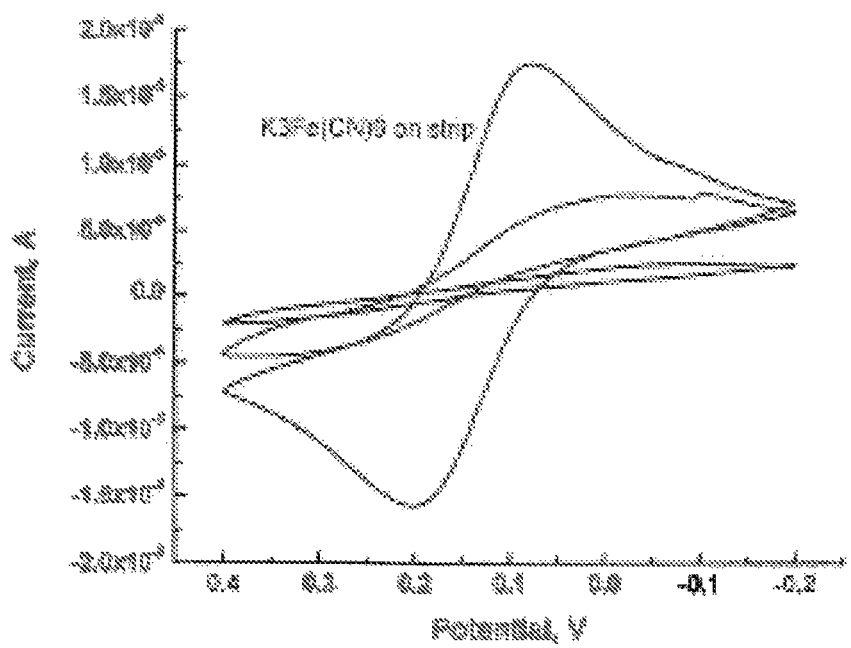
FIG. 5 depicts according to another embodiment, (A) cyclic voltammograms of a Whatmann grade 113 filter paper strip with PBS or PBS with 50 mM ferricyanide (Fe(CN)6); (B) a current versus time plot for a Whatmann grade 113 filter paper in the presence of PBS and 50 mM Fe(CN)6; (C) cyclic voltammograms of a 2.0% fibrin clot in Whatmann grade 113 filter paper in the presence of PBS with 50 mM Fe(CN)6 in the presence and absence of plasmin; (D) a current versus time plot for a 2.0% fibrin clot in Whatmann grade 113 filter paper in the presence of PBS and 50 mM Fe(CN)6 and in the presence and absence of plasmin; (E) a cyclic voltammogram of a fibrin clot in the presence (blue) and absence (red) of plasmin (Scan rate=0.1V/sec); (F) a current vs time (i-t) response of a firbin clot in the presence (red) and absence (blue) of plasmin (Potential=−50 mV); (G). a linear Scan Voltammogram of a fibrin clot in the presence (blue) and absence (red) of plasmin (Scan rate=0.1V/sec).
Figure 5:
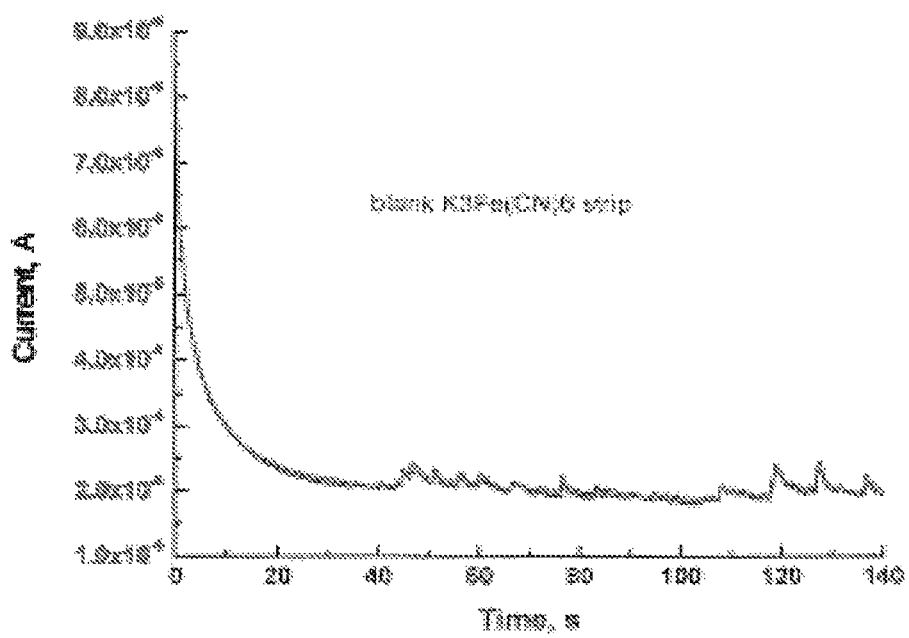
Figure 5:
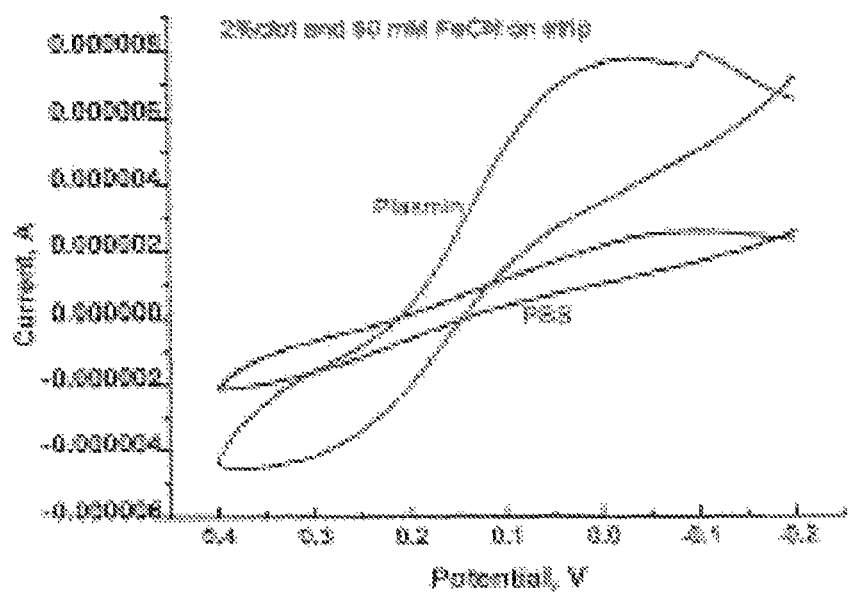
Figure 5:
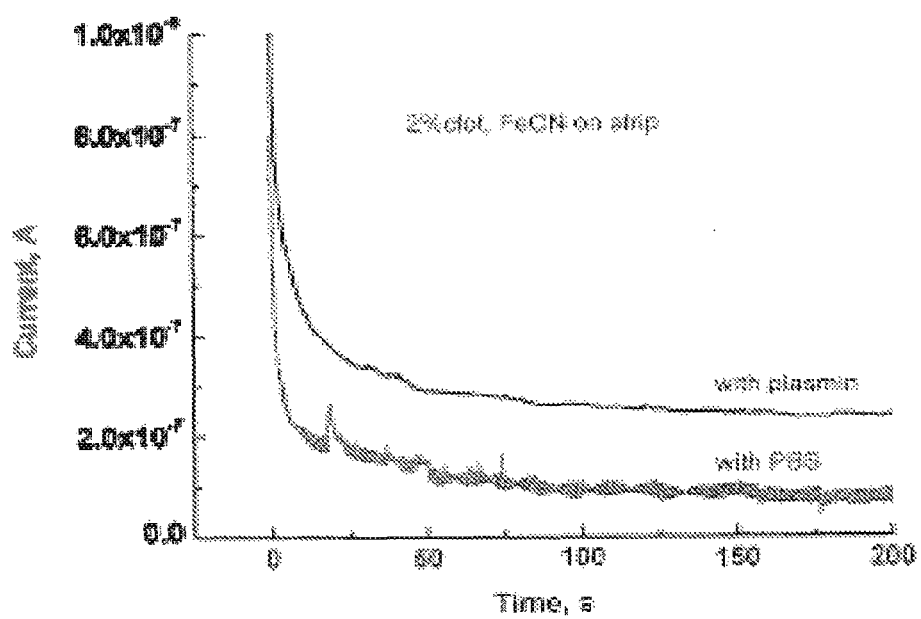
Figure 5:
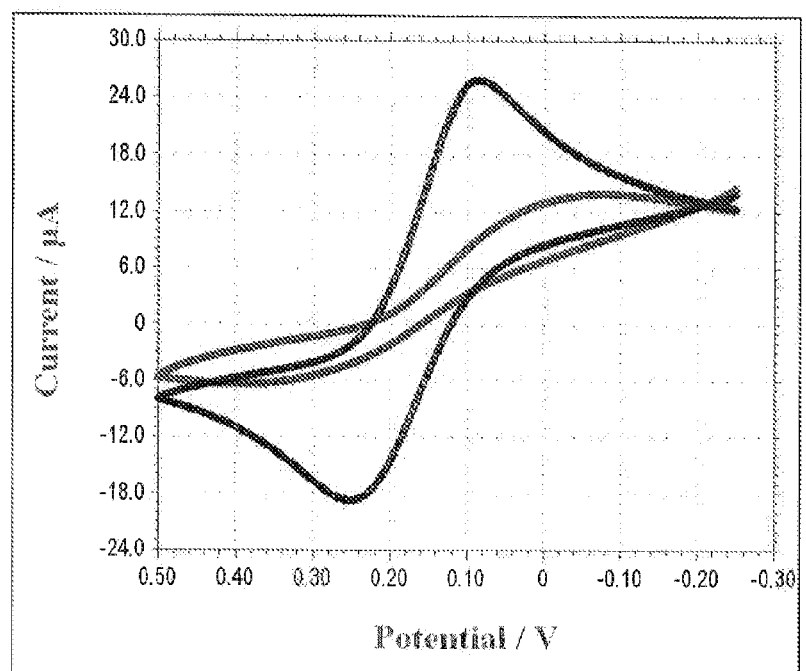
Figure 5:
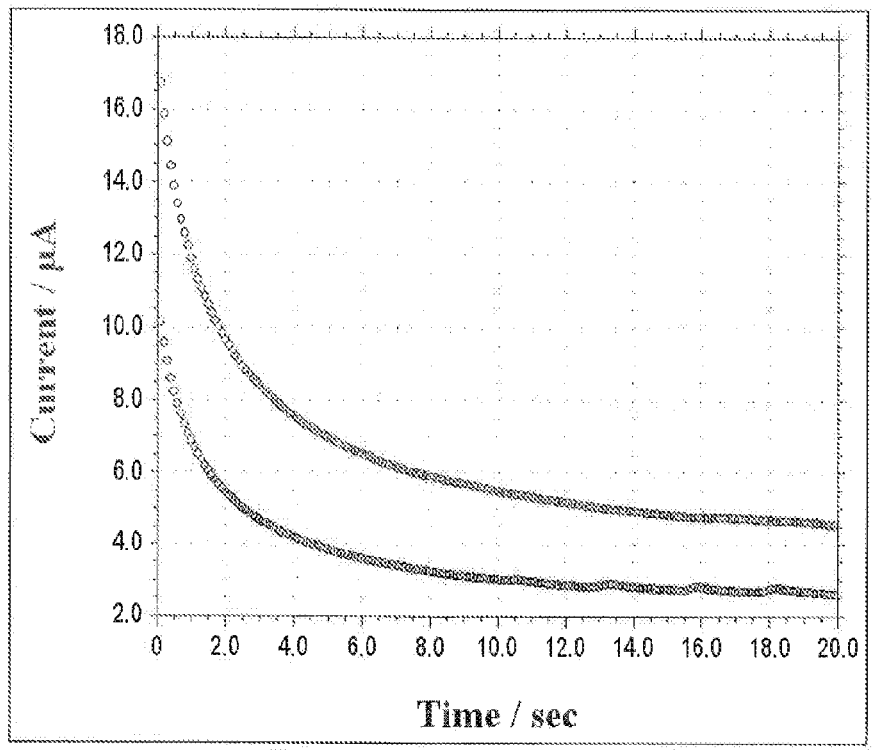
Figure 5:
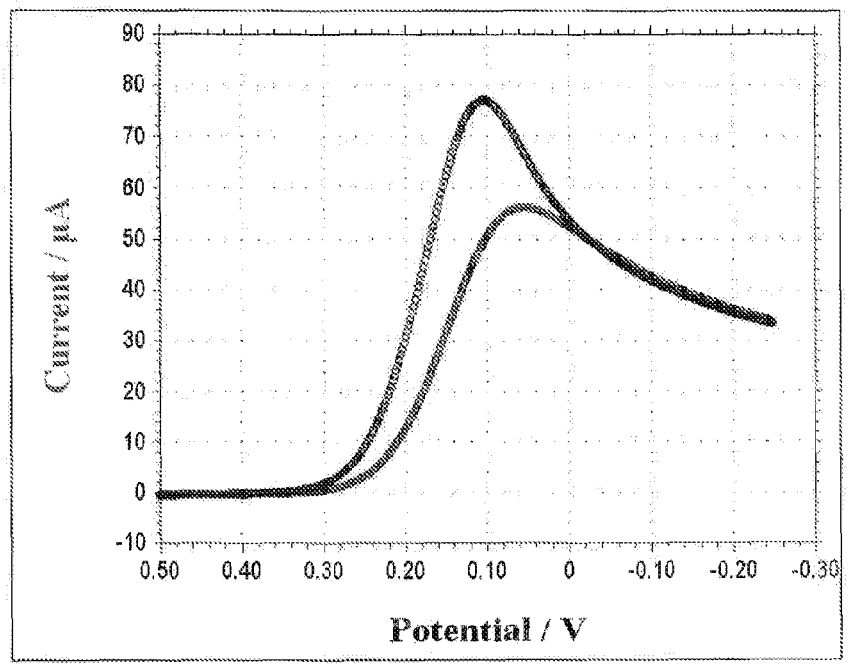

The second potential is typically supplied by a controllable variable potential source connected to the counter electrode (or the auxiliary electrode in embodiments where the counter electrode comprises a reference and auxiliary electrode), such as those known in the art or commercially available potential sources. The data storage unit stores the recorded current values. In one embodiment comprises a commercially available memory circuit. The processing unit is used to analyze the stored current values using a predetermined mathematical model. The result of the analysis is presented, via a display or the like, such as the voltammograms or current versus time plots presented in FIGS. 4 and 5.

In one embodiment, the working electrode, the counter electrode, the current measurement unit, and the control unit are integrated as a single device arranged to output the measured current values to an internal or external data storage and processing unit. The control unit may be externally controlled by an external data storage and processing unit. Accordingly, an inexpensive and versatile system for detecting or monitoring proteolysis of proteinaceous matrices capable of field use or point of care use is contemplated.

In some embodiments the systems of the various embodiment are designed for detecting or monitoring the proteolysis of particular proteinaceous matrices such as fibrin clots, collagen matrix, or gelatin. In these embodiments the systems are preferably fully integrated, i.e., the proteinaceous matrix, the working electrode, the counter electrode, the current measurement unit, the control unit, the data storage unit and the processing unit are integrated as one device. The device may be arranged to output the result from the analysis.

According to various embodiments, the data processing and output units are one of hardware, software, firmware, or combinations thereof. In certain embodiments, the data processing and output units are adapted from and incorporated as mobile devices, such as smart phone devices. In other embodiments, the data processing and output units are implemented as mobile apps compatible with one or more smart phone devices, including without limitation IOS phones, Android phones and similar smart phone devices.

According to additional embodiments, the data processing and output units are connected to the measuring apparatus via cloud, other wired or wireless communication networks, or other remote communication means.

In other embodiments, there are also provided kits for practicing the aforementioned methods. Typically, kits for carrying out the methods of the present invention contain all the necessary reagents to carry out the method. For example, in one embodiment a kit may comprise a support comprising a proteinaceous matrix or a support and the necessary reagent to form a protein matrix on the support such as a solution of fibrinogen and thrombin. The kit may also comprise any one or more of: (1) at least one electrode, (2) at least one electroactive species, (3) at least one electrolytic solution, (4) at least one salt and (5) at least one control sample with a known level of proteolytic activity.

The kit can also feature printed instructions for using the kit to qualitatively or quantitatively detect or monitor the proteolysis of a protein matrix in accordance with the present invention.

3. Alternative System and Method Based on AC-Based Voltammetric and Spectroscopic Techniques In alternative embodiments, the inhibited diffusion of elactomers in protein matrices enables the use of other measurement techniques based on alternating currents (AC) or multiple DC pulses. In these embodiments, the elactomer reactant may diffuse back and forth from the electrode surface with every change in voltage polarity or amplitude, thereby effectively lengthening the diffusion lengths and exaggerating the differences in diffusion coefficient in pristine or proteolyzed matrices.

With multiple pulse voltammetry voltage pulses of magnitude, which allows electrochemical reaction (working pulses) are alternated with pulses where no reaction takes place (resting pulses). During the resting pulses elactomer reactants diffuse towards the electrode surface without being consumed, while elactomer products diffuse away from electrode. The measured quantity is the Faradaic current at the n-th pulse of working voltage.

As a limiting condition for a fast-diffusing electroactive species and low frequency, full equilibration of electrode-surface concentrations can take place, so that the measured current is substantially the same at every pulse, corrected for whatever small change in bulk concentration ($C_0$) is observed. On the other end, with slow-diffusing electroactive species and high frequency no recovery whatsoever occurs at the electrode surface and the current diminishes at every pulse, resembling the decay observed with chrono-amperometry. The highest sensitivity of the technique may be achieved between these two limiting conditions, and may be determined experimentally according to certain embodiments.

In a further embodiment, there are employed spectroscopic techniques, such as electrochemical impedance spectroscopy (EIS), in the system and method of this disclosure. According to this embodiment, changes in diffusivity may be observed in the frequency domain. Frequency-based measurements are generally more sensitive and accurate than amplitude-based techniques, and thus provide further benefit to the system and method according to this embodiment.

The same physical phenomena of diffusion to and away from the working electrode surface apply with EIS as with the pulsed technique described herein. However, in this embodiment, the frequency is varied during the course of the measurement. For a specific diffusion constant there is a specific frequency, where inhibition of diffusion causes the Farradaic current to lag the voltage waveform the most, also known as Warburg Impedance. In a frequency domain measurement according to one embodiment, this frequency may correspond to the peak phase delay and be a measure of the diffusion coefficient, and hence the degree of proteolysis in the matrix.

IV. Examples

Below description is provided as an example of certain embodiments, and is not to limit the scope of the various embodiments of this disclosure.

Example 1

Voltammetric Measurement of Proteolysis

Human fibrinogen and human thrombin stock solutions are mixed to yield 10 μL final solution (2% fibrinogen+0.1 U of thrombin final concentrations), which was vortexed and immediately applied to a 5×5 mm filter paper strip (Whatman No. 4, with large pore size, 30-40 μm particle retention). A fibrin clot was formed within the pores of the paper strip, and the strip left to dry at room temperature for two hours. Due to the fibrinogen concentration, the clot pore-sizes are smaller than the pores in the filter paper.

Figure 1:
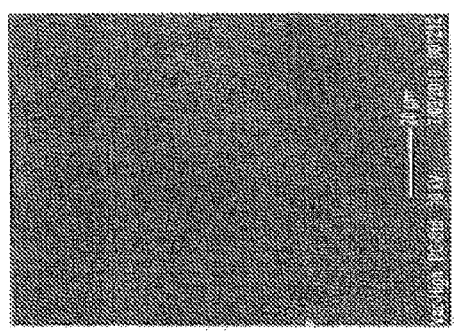
FIG. 1 depicts according to one embodiment of this disclosure, (A) an electron micrograph of the surface of a gold electrode, scale bar is 20 μm; (B) an electron micrograph of the surface a gold electrode with a 2% fibrin clot in 1×PBS (phosphate buffered saline: 137 mM NaCl, 2.7 mM KCl, 10 mM sodium phosphate dibasic, 2 mM potassium phosphate monobasic and a pH of 7.4) on the electrode surface, scale bar is 20 μm; (C) an electron micrograph of the surface of a gold electrode with a 2% fibrin clot in 0.1×PBS (13.7 mM NaCl, 0.27 mM KCl, 1 mM sodium phosphate dibasic, 0.2 mM potassium phosphate monobasic and a pH of 7.4) on the electrode surface, scale bar is 10 μm; (D) Image of a sensor chip with multiple electrodes. Shown is the placement of a filter containing human fibrin clot.
Figure 1:
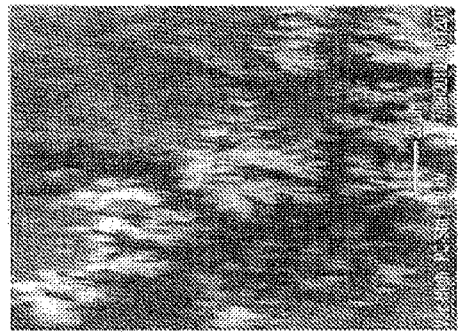
Figure 1:
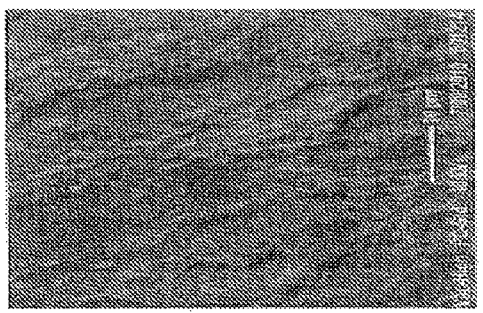
Figure 1:
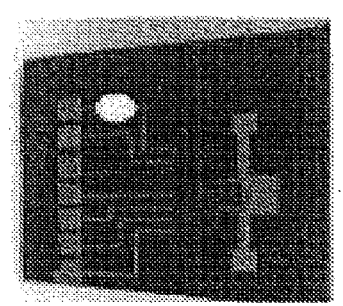
Figure 2:
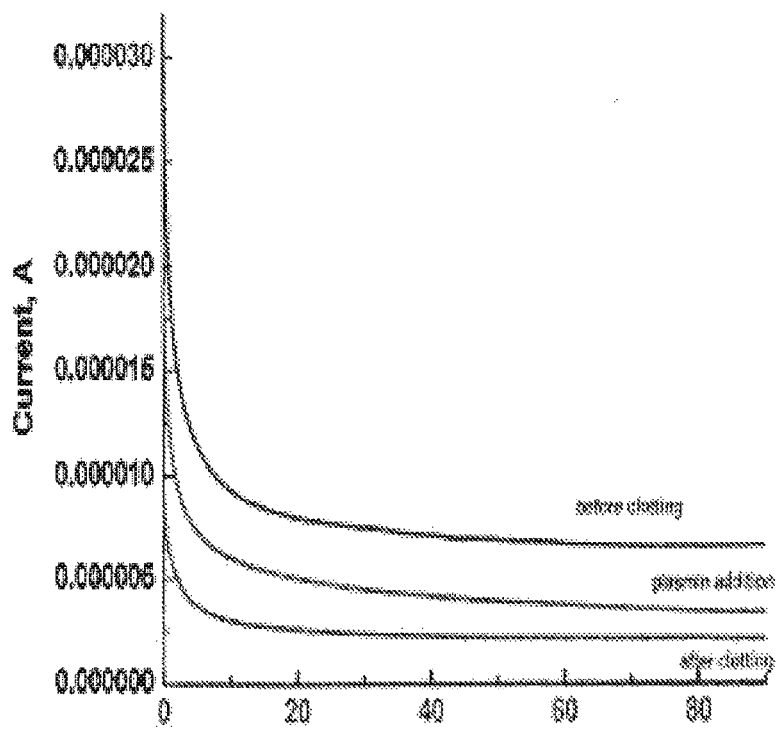
FIG. 2 depicts according to another embodiment, (A) a current versus time plot for a blank gold electrode, a gold electrode with a fibrin clot on the surface and the gold electrode with the fibrin clot after incubation with plasmin for 7 minutes; (B) a table setting out the amperometric response of the gold electrode, the gold electrode with a fibrin clot and the gold electrode with the fibrin clot after incubation with plasmin for 7 minutes; (C) the increase in current over time after the addition of plasmin to a fibrin clot on a gold electrode; and (D) the increase in current over time after the addition of 87 nM plasmin to a 15 μl clot formed on a gold electrode formed with 2% fibrinogen and 1 unit thrombin.
Figure 2:
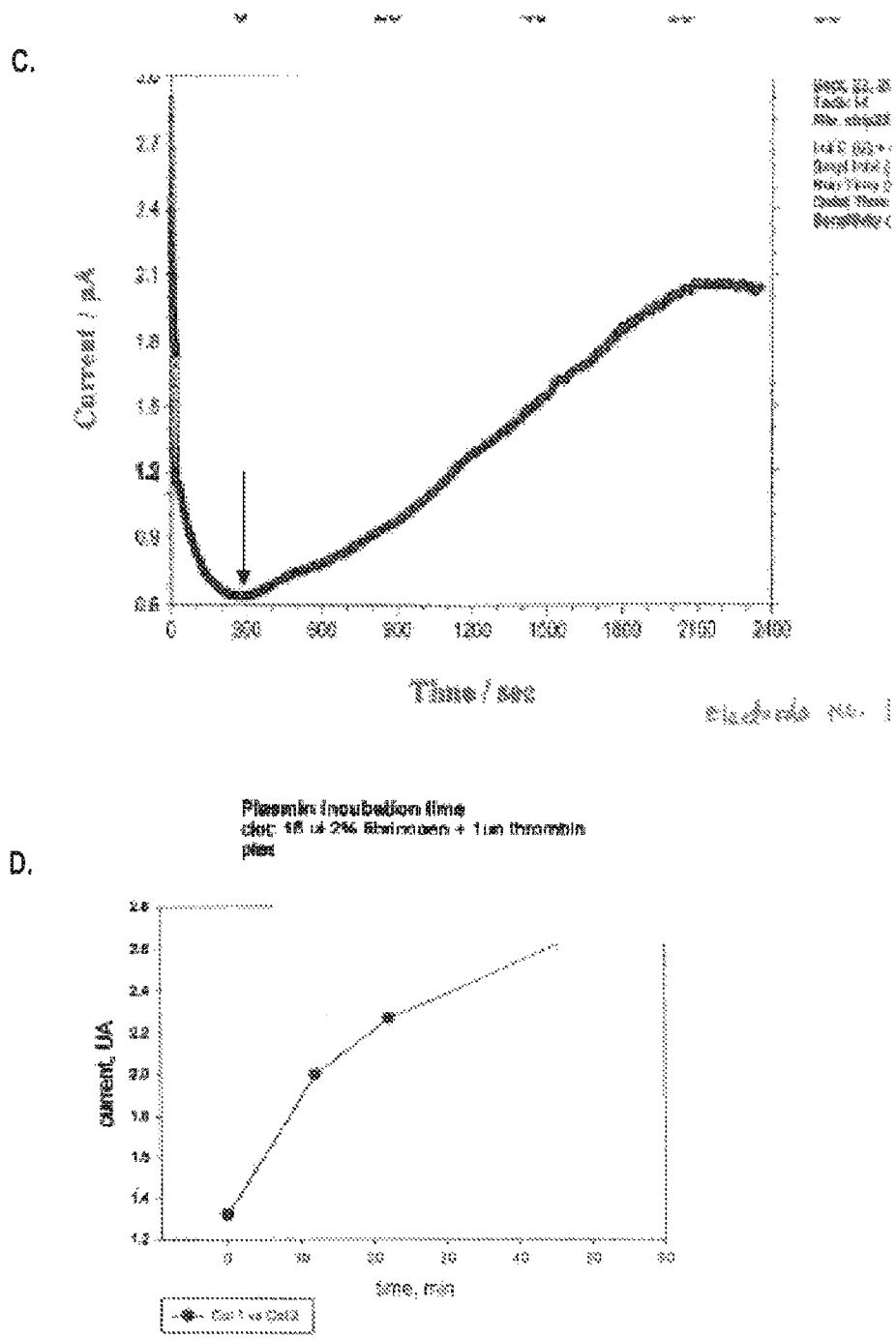
Figure 3:
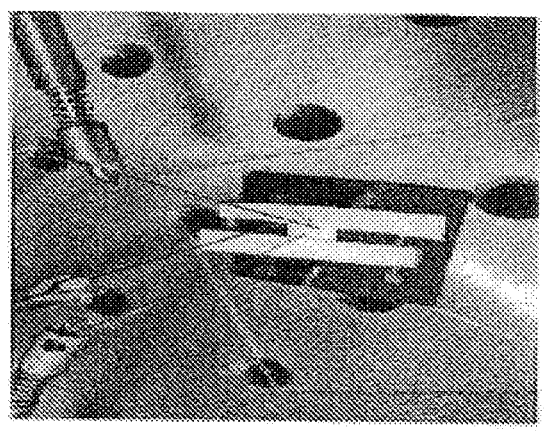
FIG. 3 depicts according to another embodiment, (A) part of a system of the disclosure comprising three electrodes wherein the electrodes are in contact with a fibrin clot formed in a 5×5 mm strip of Whatmann grade 113 filter paper with a pore size of approximately 30 μm. (B) Strips of filterpaper containing human fibrin clot and impregnated with K3Fe(CN)6. (C) a filter strip impregnated with a fibrin clot and K3Fe(CN)6 and attached to a sensor chip with printed gold electrodes. Seen are the probe tips for electrical contact to a measurement instrument (potentiostat in this case) and a reference silver wire electrode.
Figure 3:
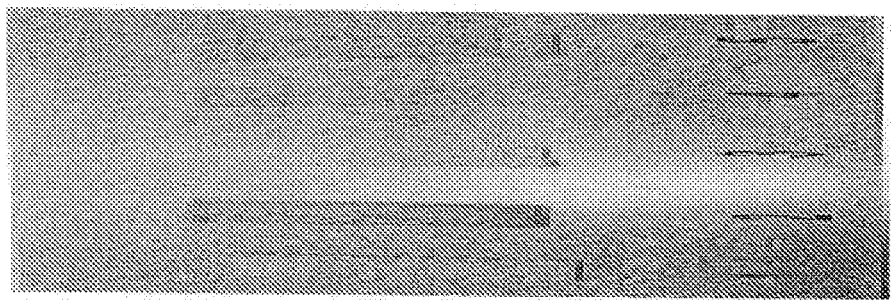
Figure 3:
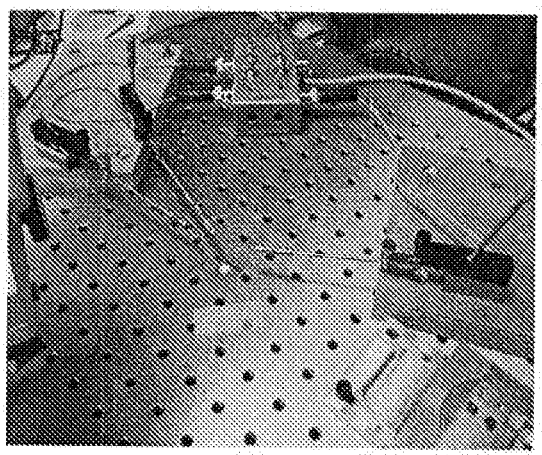

The strip-clot was impregnated with a solution of 50 mM $K_3Fe(CN)_6$, containing 0.2% Tween 20, and left to dry. The strip was attached to a chip containing flat printed electrodes (either gold or conductive carbon). An optional silver wire can attached to the strip as a reference electrode (FIG. 3C). The strip is rehydrated with a phosphate-buffered saline physiological solution (PBS), containing 2 nM human plasmin PBS without plasmin is used as a control. Electrochemical tests were performed on the strip to determine the electrochemical current arising from reduction of $K_3Fe(CN)_6$ to $K_2Fe(CN)_6$. The current response (FIGS. 5E, F, G) is a function of several parameters: potential, electrode area, $K_3Fe(CN)_6$ concentration and diffusion coefficient.

Example 2

CES and WES Used for Chronoamperometry

Refer to the aforementioned mixed composition of the WES and CES employed for chronoamperometry measurements. As an example, in the Fc-PEG elactomer discussed above, the electroactive Fc moiety has a standard electrode potential $E0$ of +0.641V, and elactomer itself has even higher $E0$, given the pi-electron in the amide bond (measured $E0$ is in the +0.7V to 0.75V range). If the reduced form of the WES is used for measurement at the WE, this high resistance to oxidation—relative to other commonly used electroactive species—provides tolerance to a number of oxidizing CES. Nevertheless, due to the concentration excess of CES, as discussed above, it is advantageous use a weak oxidizer as the CES, so that the WES exists predominantly in its reduced state.

Accordingly, as an example, an appropriate CES is ruthenium (III) hexamine, $Ru(NH3)63+$, which has standard electrode potential $E0$ of +0.1V. Based on the Nernst equation, a WES-CES composition comprising 2 mM reduced PEG-Fc WES and 8 mM $Ru(NH_3)_6^{3+}$ CES would oxidize less than 3% of the WES. The excess of CES, coupled with its higher diffusivity provides sufficient current at the counter electrode, so that the overall current through the system is constrained only by the diffusion of elactomer WES to the WE surface. Another example of CES is the oxidized form of $Fe_3(CN)_6^{3+}$.

Figure 7:
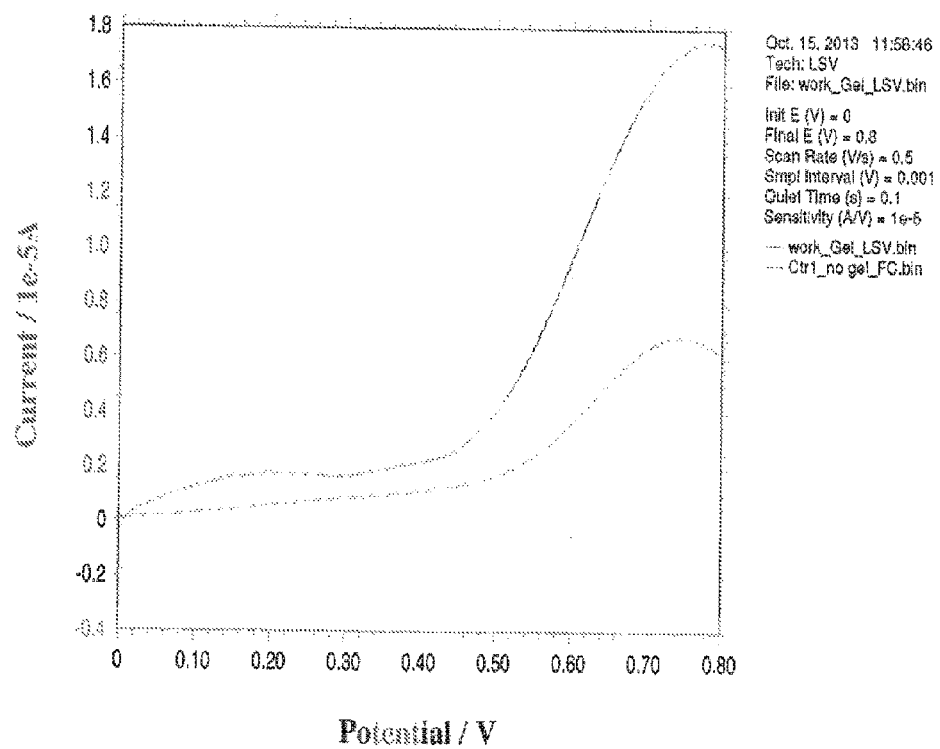
FIG. 7 depicts according to another embodiment, the linear sweep voltammetry (LSV) scan of the diffusion of a PEG polymer across a gelatin matrix/hydrogel.
Figure 8:
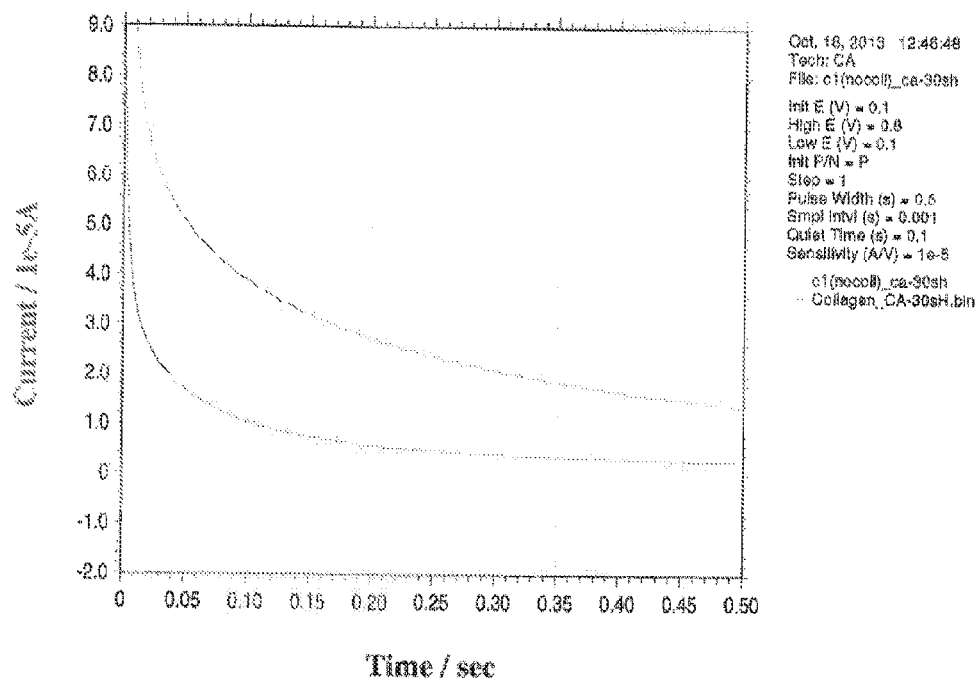
FIG. 8 depicts according to an alternative embodiment, the chronoamperometry (CA) scan of the diffusion of a PEG polymer across a gelatin matrix/hydrogel.

A composition CES-WES mixture is added to a preheated 20% solution of gelatin and deposited onto a test strip containing two screen-printed carbon electrodes. The dimensions of the electrodes exposed to the sample cell are WE 1.79×1.3 mm, and CE 0.6×1.3 mm Separate test strips without gelatin are prepared as controls. 0.8 microliters of physiologically-buffered saline are added to the strips, and the strips were assayed with linear scanning voltammetry and chronoamperometry. The results as shown in FIGS. 7 and 8 respectively, demonstrating the inhibited diffusion-limited current on the strip that contains gelatin versus the control.

From the chronoamperometric measurement, the effective diffusion coefficients (D) are calculated using Cottrell's equation. For the control strip D is $5.15 \times 10^{-6}$ cm$^2$/s, which is in line for the diffusion of a 5 kDa molecule in aqueous solution. For the gelatin strip, the effective diffusion coefficient was more than thirty times lower at $1.56 \times 10^{-7}$ cm$^2$/s. Such substantial differences in D cannot be achieved without the use of elactomer WES.

The descriptions of the various embodiments provided herein, including the various figures and examples, are to exemplify and not to limit the invention and the various embodiments thereof.

I claim:

1. An apparatus for detecting or monitoring proteolysis of a protein matrix, comprising (i) a synthetic protein matrix, (ii) a working electrode, (iii) a counter electrode, (iv) an elactomer, and (v) a small molecule electroactive species;

wherein the synthetic protein matrix is in contact with at least a portion of the working electrode or the counter electrode;

wherein the elactomer comprises a ferrocene-derivitized polymer wherein the polymer is selected from the group consisting of polyethylene glycol (PEG), polyvinyl alcohol (PVA), polyvinyl pirrolidone (PVP), and derivatives thereof;

wherein the elactomer and the small molecule electroactive species are of an opposing oxidation state and are provided in contact with the synthetic protein matrix by diffusion within and across pores of the synthetic protein matrix;

wherein the elactomer is capable of generating diffusion-limited electrochemical currents at the working electrode and the small molecule electroactive species is capable of generating counter currents at the counter electrode; and wherein the diffusion limited electrochemical currents are indicative of a level of proteolysis of the synthetic protein matrix.

2. The apparatus of claim 1, wherein the synthetic protein matrix is selected from the group consisting of a fibrin clot, platelet rich plasma clot, gelatin, and a collagen matrix, and wherein the matrix is formed on, within, or around a support.

3. The apparatus of claim 1, wherein the working electrode is larger than the counter electrode.

4. The apparatus of claim 1, wherein the relative concentrations of the elactomer and the small molecule electroactive species are determined such that essentially all of the current at the working electrode are generated by the elactomer, and not by the small molecule electroactive species.

5. The apparatus of claim 1, wherein the elactomer is a ferrocene-derivitized polyethylene glycol having the formula Fc-CO—NH—$(CH_2CH_2O)_n$—NH—CO-Fc and the small molecule electroactive species is ruthenium (III) hexamine $(Ru(NH_3)_6^{3+})$.

6. The apparatus of claim 1, further comprising a sample, wherein the sample is selected from the group consisting of blood, plasma, interstitial fluid, other bodily fluid, and a control with known proteolytic activity.

7. The apparatus of claim 1, further comprising a data processing unit for analyzing diffusion limited currents using a predetermined formula or methodology, thereby producing a result indicative of proteolysis of the protein matrix.

8. The apparatus of claim 7, further comprising an output unit for the output of measurement of the diffusion limited currents and the result indicative of proteolysis.

9. The apparatus of claim 8, wherein a mobile device, a mobile application, or both comprises at least one of the data processing unit and the output unit.

10. The apparatus of claim 1, where the counter electrode comprises a reference electrode and an auxiliary electrode.

11. The apparatus of claim 1, wherein the elactomer is a ferrocene-derivitized polyethylene glycol having the formula Fc-CO—NH—$(CH_2CH_2O)_n$—NH—CO-Fc.

12. The apparatus of claim 1, wherein the small molecule electroactive species is ruthenium (III) hexamine $(Ru(NH_3)_6^{3+})$.

13. A method for detecting or monitoring proteolytic activity of a sample, comprising:
(i) providing a synthetic protein matrix subject to the proteolytic activity, wherein the synthetic protein matrix is in contact with at least a portion of a working electrode or a counter electrode;
(ii) providing an elactomer and a small molecule electroactive species in contact with the synthetic protein matrix, wherein the elactomer comprises a ferrocene-derivitized polymer wherein the polymer is selected from the group consisting of polyethylene glycol (PEG), polyvinyl alcohol (PVA), polyvinyl pirrolidone (PVP), and derivatives thereof, and the elactomer and the small molecule electroactive species are of an opposing oxidation state and are provided in contact with the synthetic protein matrix by diffusion within and across pores of the synthetic protein matrix;
(iii) exposing the synthetic protein matrix to a sample, whereby diffusion-limited electrochemical currents are generated by the elactomer at the working electrode and counter currents are generated by the small molecule electroactive species at the counter electrode; and
(iv) measuring the diffusion-limited electrochemical currents, wherein the measurement is indicative of a level of proteolytic activity in the sample.

14. The method of claim 13, wherein the measuring is performed by chronoamperometry, potential step voltammetry, linear sweep voltammetry, cyclic voltammetry, square wave voltammetry, staircase voltammetry, anodic or cathodic stripping voltammetry, adsorptive stripping voltammetry, alternating current voltammetry, rotated electrode voltammetry, normal or differential pulse voltammetry, or chronocoulometry.

15. The method of claim 14, wherein alternating currents or multiple direct current pulses are measured.

16. The method of claim 15, wherein the measuring is based on electrochemical impedance spectroscopy, and wherein changes in a frequency domain are indicative of a level of the proteolytic activity in the sample.

17. The method of claim 13, wherein the sample is selected from the group consisting of blood, plasma, interstitial fluid, and a control with known proteolytic activity.

18. The method of claim 13, wherein the elactomer is a ferrocene derivitized polyethylene glycol having the formula (Fc-CO—NH—$(CH_2CH_2O)_n$-NH—CO-Fc) and the small molecule electroactive species is ruthenium (III) hexamine $(Ru(NH_3)_6^{3+})$.

19. The method of claim 13, wherein the measurement is indicative of a baseline, and the method further comprises exposing a second synthetic protein matrix to a second sample, and measuring diffusion-limited electrochemical currents from the second sample, wherein differences between the second measurement and the baseline are indicative of changes in proteolytic activities.

20. A method for detecting or monitoring fibrinolytic activity of a sample, comprising:
(i) providing a synthetic fibrin strip, the strip having printed thereon a working electrode and a counter electrode;
(ii) providing an elactomer and a small-molecule electroactive species in contact with the fibrin strip by diffusion within and across pores of the fibrin strip, wherein the elactomer comprises a ferrocene-derivitized polymer wherein the polymer is selected from the group consisting of polyethylene glycol (PEG), polyvinyl alcohol (PVA), polyvinyl pirrolidone (PVP), and derivatives thereof, and the elactomer and the small molecule electroactive species are of an opposing oxidation state;
(iii) exposing the fibrin strip to a sample, whereby diffusion-limited electrochemical currents are generated by the elactomer at the working electrode and counter currents are generated by the small-molecule electroactive species at the counter electrode; and (iv) measuring the diffusion-limited electrochemical currents, wherein the measurement is indicative of a level of fibrinolytic activity in the sample.

21. A method for detecting or monitoring collagenase activity of a sample, comprising:
  (i) providing a gelatin strip, the gelatin strip having printed thereon a working electrode and a counter electrode;
  (ii) providing an elactomer and a small-molecule electroactive species in contact with the gelatin strip by diffusion within and across pores of the gelatin strip, wherein the elactomer comprises a ferrocene-derivitized polymer wherein the polymer is selected from the group consisting of polyethylene glycol (PEG), polyvinyl alcohol (PVA), polyvinyl pirrolidone (PVP), and derivatives thereof, and the elactomer and the small molecule electroactive species are of an opposing oxidation state;
  (iii) exposing the gelatin strip to a sample, whereby diffusion-limited electrochemical currents are generated by the elactomer at the working electrode while counter currents are generated by the small-molecule electroactive species at the counter electrode; and
  (iv) measuring the diffusion-limited electrochemical currents, wherein the measurement is indicative of a level of collagenase activity in the sample.

* * * * *